United States Patent
Goueli

(10) Patent No.: US 6,610,657 B1
(45) Date of Patent: Aug. 26, 2003

(54) ALKYL PEPTIDE AMIDES AND APPLICATIONS

(75) Inventor: Said A. Goueli, Madison, WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 09/630,115

(22) Filed: Aug. 1, 2000

Related U.S. Application Data

(62) Division of application No. 09/308,507, filed as application No. PCT/US97/21509 on Nov. 20, 1997.
(60) Provisional application No. 60/031,428, filed on Nov. 21, 1996.

(51) Int. Cl.[7] .............................................. A61K 38/10
(52) U.S. Cl. ............................. 514/14; 514/12; 514/13; 530/326; 530/327
(58) Field of Search ...................... 514/12–14

(56) References Cited

U.S. PATENT DOCUMENTS

| | | | |
|---|---|---|---|
| 5,358,934 A | * 10/1994 | Borovsky et al. | 514/17 |
| 5,453,354 A | * 9/1995 | Akerlof et al. | 435/2 |
| 5,744,354 A | * 4/1998 | Lockerbie et al. | 435/325 |
| 6,011,013 A | * 1/2000 | Carr et al. | 514/13 |
| 6,011,015 A | * 1/2000 | Vinson et al. | 514/16 |

FOREIGN PATENT DOCUMENTS

| | | |
|---|---|---|
| EP | 511600 A2 * | 4/1992 |
| WO | WO 98/22122 | 5/1999 |

OTHER PUBLICATIONS

Cosson, M. et al. Cell Motil. Cytoskeleton (1988), 10(4), 518–27.*
Si et al. Mol. Androl. (1996), 8(3,4), 235–249.*
Fenichel et al. Biol. Reprod. (1996), 54(6), 1405–1411*
Carrera et al. Dev. Biol. (1994), 165(1), 272–84.*
Chen, et al., "Organelle–specific Targeting of Protein Kinase AII (PKAII)", *Journal of Biological Chemistry*, vol. 272, 24: 15247–15257, 1997.
Dell'Acqua, et al., "Protein Kinase A Anchoring", *Journal of Biological Chemistry*, vol. 272, 20: 12881–12884, 1997.
Han, et al., "Molecular Characterization of a Novel A Kinase Anchor Protein from *Drosophila melanogaster*", *Journal of Biological Chemistry*, vol. 272, 42:26611–26619, 1997.
Huang, et al., "Identification of a Novel Protein Kinase A Anchoring Protein That Binds Both Type I and Type II Regulatory Subunits", *Journal of Biological Chemistry*, vol. 272, 12: 8057–8064, 1997.
Huang, et al., "D–AKAP2, a novel protein kinase A anchoring protein with a putative RGS domain", *Proc. Nat'l Acad. Sci. USA*, vol. 94, 11184–11189, 1997.
Leusen et al., "Inhibition of neutrophil nadph oxidase assembly by myristoylated inhibitor peptides of protein kinase C and protein kinase A", Keystone Symposium on Phosphorylation/Dephosphorylation in signal transduction, Keystone CO USA, Jan. 17–24, 1993, *J. Cell Biochem. Suppl 0* (17 part A).
Newlon, et al., "The A–kinase Anchoring Domain of Type IIα cAMP–dependent Protein Kinase is Highly Helical", *Journal of Biological Chemistry*, vol. 272, 38: 23637–23644, 1997.
A.L. Lehninger, *Principals of Biochemistry*, Worth Publishers, Inc., 1982, p. 101.

(List continued on next page.)

Primary Examiner—Michael Borin
(74) Attorney, Agent, or Firm—Michael Best & Friedrich LLP; Grady J. Frenchick; Jill A. Fahrlander

(57) ABSTRACT

Disclosed are alkyl peptide amides capable of inhibiting or reducing sperm cell motility. Methods of inhibiting or reducing sperm motility using certain alkyl peptide amides are also disclosed.

7 Claims, 10 Drawing Sheets

OTHER PUBLICATIONS

Figure 1:
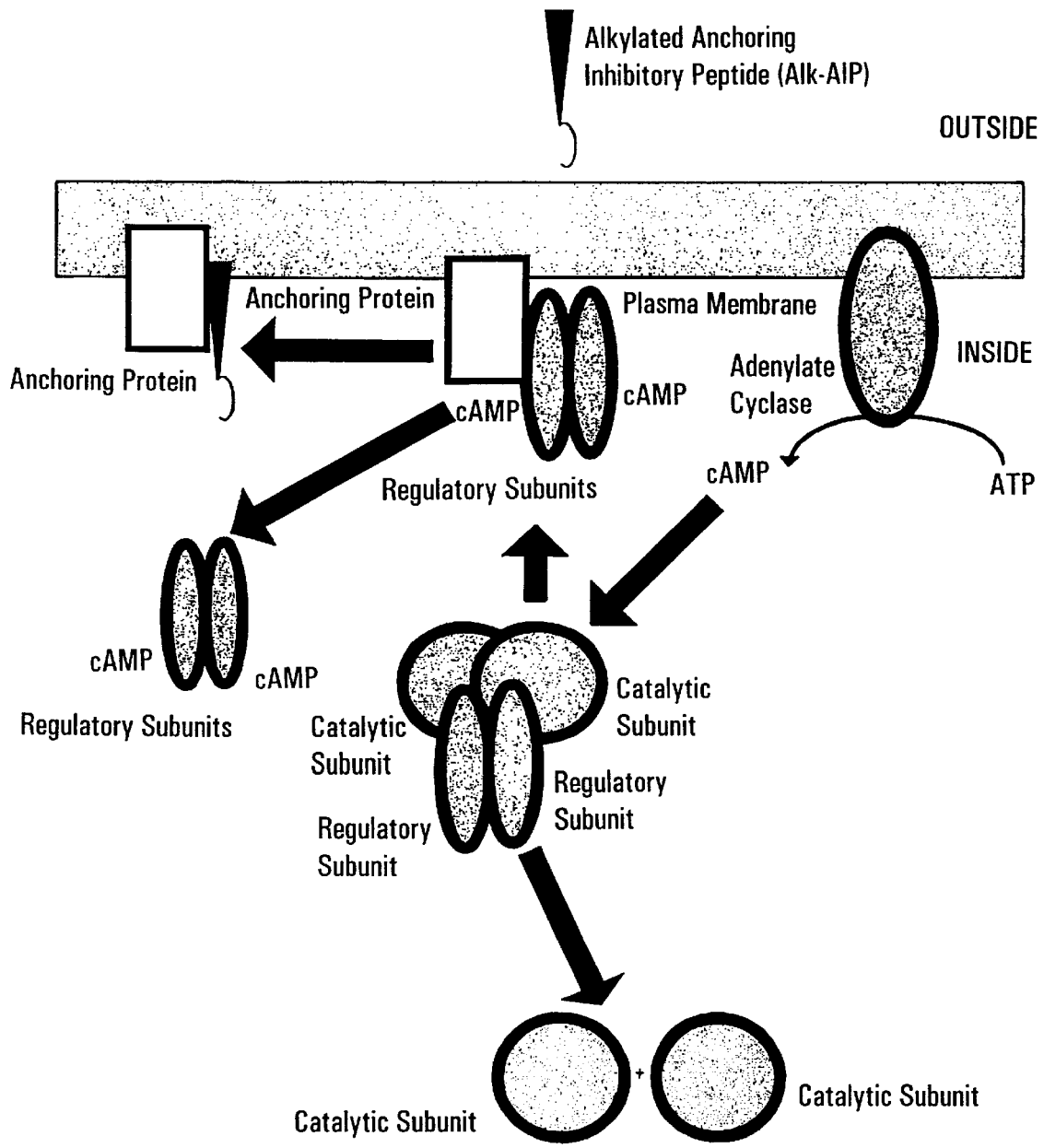

Babcock et al., *J. Biol. Chem.* 251:3881–3886, 1976.
Bedford, and Hoskins, In Marshall's *Physiology of Reproduction,* Lamming, ed., pp. 379.
Carr et al., *J. Biol. Chem.* 266:14188–14192, 1991.
Carr et al., *J. Biol. Chem.* 267:16816–16823, 1992.
Carr et al., *J. Biol. Chem.* 267:13376–13382, 1992.
Carr et al., *J. Biol. Chem.* 267(19):13376, 1992.
Carr and Scott, *Trends Biochem. Sci.* 17:246–249, 1992.
Carr et al., *J. Biol. Chem.* 268:20729–20732, 1993.
Carr and Acott, *Biology of Reproduction* 43:795–805, 1990.
Carrera et al., *Dev. Biol.* 165:272–284, 1994.
Coghlan et al., *J. Biol. Chem.* 269:7658–7665, 1994.
De Camilli et al., *J. Cell Biol.* 103:189–203, 1986.
Eichholtz et al., *J. Biol. Chem.,* 268: 1982–1986, 1993.
Eisenberg et al., *Proc. Natl. Acad. Sci.* USA 81:140–144, 1984.
Garbers and Kopf, in *Advances in Cyclic Nucleotide Research,* Greengard and Robinson, eds., vol. 13, pp. 252–306, Raven Press, New York, 1980.
Garbers et al., Adv. Cuclic Nucleotide Res. 9:583–595, 1978.
Garbers et al., *Biol. Reprod.* 7:132, 1972.
Goueli et al. (1995) *Anal. Biochemistry* 225:10–17.
Hausken et al., J. Biol. Chem. 269:24245–24251, 1994.
Horowitz et al., J. Biol. Chem. 263:2098–2104, 1988.
Hoskins et al., Biol. Reprod. 13:168–176, 1975.
Hoskins, Journal of Biological Chemistry 248:1135–1140, 1973.
Hoskins et al., J. Reprod. Fertil. 37:131–133, 1974.
Hubbard and Cohen, Trends Biochem. Sct. 18:172–177, 1993.
Johnson et al., Proc. Natl. Acad. Sci. USA 91:11492–11496, 1994.
Klauck et al., *Science* 271:1589–1592, 1996.
Kopf and Gerton, ij Elements of mammalian Fertilization, Wassermann, ed., pp. 153–203, CRC Press, Boca Raton, Florida, 1991.
Lee and Storey, Biol. Reprod. 34:349–356, 1986.
Li and Rubin, *J. Biol. Chem.* 270:1935–1944, 1995.
Lieberman et al.. J. Cell Biol. 107:1809–1816, 1988.
Lin et al., *J. Biol Chem.* 270:27804–27811, 1995.
Lindemann and Kanous. *Arch. Androl.* 23:1–22, 1989.
Liotta et at., J. Biol. Chem. 269:22996–23001, 1994.
Luo et al., *J. Biol. Chem.* 265:21804–21810, 1990.
Merrifield, J. *Amer. Chem. Soc.* 85:2149–2156, 1963.
McCartney et al., J. Biol. Chem. 270:9327–9333, 1995.
Mochly–Rosen, Science 268:247–251, 1995.
Noland et al., *Biol. Reprod.* 37:171–180, 1987.
O'Brian et al., *Biochem. Pharmacol* 39:49–57, 1990.
Okamura et al., *J. Biol. Chem.* 260:9699–9705, 1985.
Pariset and Weinman, *Mol. Reprod. Develop.* 39:415–422, 1994.
Paupard et al., *J. Cell Biochem.* 37:161–175, 1988.
Rosenmund et al., *Nature* 368:853–856, 1994.
Rubin, *Biochem. Biophys.* Acts 1224:467–479, 1994.
San Agustin and Witman, *Cell Motility & the Cytoskeleton* 27:205–18, 1994.
Satir, Modern Cell Biol. 4:1–46, 1985.
Scott et al., *J .Biol. Chem.* 265:21561–21566, 1990.
Scott and Carr, News Physciol. Sci. 7:143–148, 1992.
Shaw, C., Methods in Molecular Biology 32:275–287, 1994.
Smith et al., Biol. Reprod. 54:719–727, 1996.
Stephens et al., *Biol. Reprod.* 38:577–586, 1988.
Tash et al., *Cell* 38:551–559, 1984.
Tash and Bracho, *J. Androl.* 15:505–509, 1994.
Tash and Means, *Prog. Clin. Biol. Res.* 267:335–355, 1988.
Tash, Cell Motil. Cytoskel. 14:332–339, 1989.
Vijayaraghavan et al., Biol. Reprod. 54:709–718, 1996.
Vijayaraghavan et al., *Mol. Reprod. Dev..* 38:326–333, 1994.
Vijayaraghavan et al., *Mol. Reprod. Develop.* 25:186–194, 1990.
Vijayaraghavan et al., *Biol. Reprod.* 40:744–751, 1989.
Vijayaraghavan and Hoskins, *Cell Calcium* 10:241–253, 1989.
Vijayaraghavan et al., *Biol. Reprod.* 32:489–500, 1985.
Vijayaraghavan and Hoskins, J. Cyclic Nucleotide Protein Phosphoryl. Res. 10:499–510, 1985.
Vijayaraghavan and Hoskins, *Biol. Reprod.* 34:468–77, 1986.
Zaliani et al. Drug Design and Discovery, 23, 63–74, Apr. 1996.*
Devadas et al. J. Biol Chem., 267, 7224–7239, Jul. 1992.*
Towler et al. PNAS, 83, 2812–2816, Nov. 1993.*
Barja P. Cellular Immunology, 153, 23–38, Jan. 1994.*
Eichholtz, T. et al. J. Biol. Chem., 268, 1982–1986, Oct. 1992.*
Schramm et al. Antiviral Research, 30, 155–170, Jan. 1996.*
Williams R.E. et al. Peptides. Proc. Eur. Pept. Symp., Leiden, Netherlands, pp. 662–663.*

* cited by examiner

SEQUENCE LISTING

<160> NUMBER OF SEQ ID NOS: 13

<210> SEQ ID NO 1
<211> LENGTH: 12
<212> TYPE: PRT
<213> ORGANISM: Homo sapiens

<400> SEQUENCE: 1

Thr Arg Asp Ile Tyr Glu Thr Asp Tyr Tyr Arg Lys
 1               5                  10

<210> SEQ ID NO 2
<211> LENGTH: 24
<212> TYPE: PRT
<213> ORGANISM: Homo sapiens

<400> SEQUENCE: 2

Asp Leu Ile Glu Glu Ala Ala Ser Arg Ile Val Asp Ala Val Ile Glu
 1               5                  10                  15

Gln Val Lys Ala Ala Gly Ala Tyr
             20

<210> SEQ ID NO 3
<211> LENGTH: 14
<212> TYPE: PRT
<213> ORGANISM: Homo sapiens

<400> SEQUENCE: 3

Leu Ile Glu Glu Ala Ala Ser Arg Ile Val Asp Ala Val Ile
 1               5                  10

<210> SEQ ID NO 4
<211> LENGTH: 14
<212> TYPE: PRT
<213> ORGANISM: Homo sapiens

<400> SEQUENCE: 4

Thr Ala Glu Glu Val Ser Ala Arg Ile Val Gln Val Val Thr
 1               5                  10

<210> SEQ ID NO 5
<211> LENGTH: 14
<212> TYPE: PRT
<213> ORGANISM: Homo sapiens

<400> SEQUENCE: 5

Leu Ile Glu Thr Ala Ser Ser Leu Val Lys Asn Ala Ile Glu
 1               5                  10

<210> SEQ ID NO 6
<211> LENGTH: 14
<212> TYPE: PRT
<213> ORGANISM: Homo sapiens

<400> SEQUENCE: 6

Leu Ile Glu Thr Ala Ser Ser Leu Val Lys Asn Ala Ile Gln
 1               5                  10

<210> SEQ ID NO 7
<211> LENGTH: 18
<212> TYPE: PRT
<213> ORGANISM: Homo sapiens

```
<400> SEQUENCE: 7

Glu Val Ala Ala Glu Val Leu Ala Glu Val Ile Thr Ala Ala Val Lys
 1               5                  10                  15
Ala Val

<210> SEQ ID NO 8
<211> LENGTH: 14
<212> TYPE: PRT
<213> ORGANISM: Homo sapiens

<400> SEQUENCE: 8

Ile Ile Asp Met Ala Ser Thr Ala Leu Lys Ser Lys Ser Gln
 1               5                  10

<210> SEQ ID NO 9
<211> LENGTH: 14
<212> TYPE: PRT
<213> ORGANISM: Homo sapiens

<400> SEQUENCE: 9

Leu Ala Glu Lys Ile Val Ala Glu Ala Ile Glu Lys Ala Glu
 1               5                  10

<210> SEQ ID NO 10
<211> LENGTH: 22
<212> TYPE: PRT
<213> ORGANISM: Homo sapiens

<400> SEQUENCE: 10

Val Ile Ser Glu Ala Thr Glu Gln Val Leu Ala Thr Thr Val Gly Lys
 1               5                  10                  15
Val Ala Gly Arg Val Cys
            20

<210> SEQ ID NO 11
<211> LENGTH: 20
<212> TYPE: PRT
<213> ORGANISM: Homo sapiens

<400> SEQUENCE: 11

Thr Thr Tyr Ala Asp Phe Ile Ala Ser Gly Arg Thr Gly Arg Arg Asn
 1               5                  10                  15
Ala Ile His Asp
            20

<210> SEQ ID NO 12
<211> LENGTH: 24
<212> TYPE: PRT
<213> ORGANISM: Homo sapiens

<400> SEQUENCE: 12

Asp Leu Ile Glu Glu Ala Ala Ser Arg Pro Val Asp Ala Val Pro Glu
 1               5                  10                  15
Gln Val Lys Ala Ala Gly Ala Tyr
            20

<210> SEQ ID NO 13
<211> LENGTH: 22
<212> TYPE: PRT
<213> ORGANISM: Homo sapiens
```

```
<400> SEQUENCE: 13

Tyr Glu Thr Leu Leu Ile Glu Thr Ala Ser Ser Leu Val Lys Asn Ala
 1               5                  10                  15

Ile Gln Leu Ser Ile Glu
            20
```

ALKYL PEPTIDE AMIDES AND APPLICATIONS

CROSS-REFERENCE TO RELATED APPLICATIONS

This application is a divisional of U.S. application Ser. No. 09/308,507 filed May 19, 1999, which claims priority to PCT Application No. PCT/US97/21509, filed Nov. 20, 1997, which claims the benefit of the priority date, under 35 U.S.C. §119, of U.S. Provisional Application No. 60/031,428, filed Nov. 21, 1996.

STATEMENT REGARDING FEDERALLY SPONSORED RESEARCH OR DEVELOPMENT

Not Applicable

BACKGROUND OF THE INVENTION

This invention pertains to compositions capable of regulating protein activity, particularly activity dependent upon binding between two or more proteins. Specifically, the invention pertains to compositions and methods for delivering a peptide inhibitor moiety into a living cell including moieties, capable of inhibiting binding between a protein kinase and at least one other protein in the cell such as anchoring proteins.

Signaling molecules, such as hormones and neurotransmitters, elicit cellular responses through interrelated biochemical reactions. A variety of specific and selective reagents have been developed, which make it possible to study how such signaling molecules mediate such cellular responses in vitro. The study of such responses is an important first step in the discovery and development of new drugs. The development of specific and selective reagents capable of being used, in similar studies in either cell culture medium or in a whole animal is of equal importance. The most preferred such reagents are, traditionally, ones which enable the study of specific processes in living cells without breaking the cell or introducing artifacts therein.

Synthetic molecules such as synthetic peptides or peptidomimetics capable of interacting with, or competing with signaling protein molecules, such as protein kinases or the insulin receptor, have been reported in the literature. Various strategies have been reported for introducing such synthetic molecules into living cells, including electroporation, osmotic shock, and permeabilization of cells using agents such as saponins, streptolysin O, or liposomes. However, those delivery systems tend to cause cellular damage. Microinjection, another known method for introducing such synthetic molecules into living cells, is less damaging, but suffers the drawback of being labor intensive.

A recent publication by Liotta et al. indicates that synthetic peptides can be modified so that they passively migrate into the membranes of living cells, where the modified peptides can interact with trans-membrane proteins (Liotta et al., *J. Biol. Chem.* 269:22996–23001, 1994). The Liotta et al. publication demonstrates that a synthetic Tris-sulfotyrosyl dodecapeptide analogue of the insulin receptor 1146-kinase domain is a good inhibitor of tyrosine dephosphorylation of the insulin receptor in situ. The most significant observation made by Liotta et al. was the fact that a particular synthetic tris-sulfotyrosyl dodecapeptide (TRDIYETDYYRK-amide) (SEQ ID NO:1), a stearyl peptide amide, caused an 4.5-fold increase in insulin-stimulated receptor autophosphorylation in intact CHO/HIRc cells. That stearyl peptide amide displayed specificity toward tyrosine-class phosphatases only, as it did not have an effect on the activities of the serine/threonine phosphatases PP-1, PP-2A, or alkaline phosphatase. Approaches similar to that of Liotta et al. but with fatty acid-peptide conjugates had been used to inhibit protein kinase C (PKC) and tyrosine kinase activities in intact cells (Eichholtz et al. *J. Biol. Chem.*, 268: 1982–1986, 1993; Liotta et al., *J. Biol. Chem.* 269(37):22996–23001, 1994; and O'Brian et al., *Biochem. Pharmacol.* 39:49–57, 1990).

One type of signaling protein molecule, signal transduction enzymes (e.g. protein kinases and phosphatases), play pivotal roles in mediating cellular responses to a wide variety of stimuli. Such enzymes are often targeted to specific substrates or cellular compartments through their interaction with cellular "anchoring proteins" (Hubbard and Cohen, *Trends Biochem. Sci.* 18:172–177, 1993). The anchoring or compartmentalization of such proteins is thought to be critical in determining the specificity of response for a particular stimulus (Scott and Carr, *News Physiol. Sci.* 7:143–148, 1992; Rubin, *Biochem. Biophys. Acta* 1224:467–479, 1994; Mochly-Rosen, *Science* 268:247–251, 1995). Anchoring of cyclic AMP-dependent protein kinase A (PKA or A-kinase) is accomplished by the binding of its regulatory subunit (R) to an amphipathic helix-binding motif located within A-kinase anchoring proteins (AKAPs) (Carr et al., *J. Biol. Chem.* 266:14188–14192, 1991).

Many different peptides have been developed and synthesized which are known to have functional activities in vitro, including peptides designed to interact with anchor proteins or other proteins known to have binding regions in the intracellular space of living cells. The protein kinase anchoring inhibitory peptides, such as Ht31, (DLIEEAASRIVDAVIEQVKAAGAY) (SEQ ID NO:2), are included in the category of peptides designed to interact with anchor proteins (Carr et al., *J. Biol. Chem.* 267(19): 13376, 1992). Ht31 has been shown to inhibit the binding of the regulatory subunit of PKA to anchoring protein using cellular extracts in vitro. The PKA regulatory subunit from which the sequence of Ht31 was derived was used to synthesize the peptide moieties of the new reagents used in several of the examples of this application. Peptides such as Ht31, which are known to inhibit PKA binding to anchor proteins, are referred to herein as "anchor inhibiting peptides" or (AIPs).

Peptides known to be functionally active in vitro have also been used to develop and synthesize inactive peptides for use as control peptides. The alterations made in the amino acid sequence of an active peptide to produce an inactive peptide are expected to have a disruptive effect on the predicted α-helix conformation of the active parent peptide, a conformation considered essential to ensure the maintenance of functional activity. Altered inactive peptides of this type have been used as controls in assaying the functional activity and other properties of the parent peptides from which they were derived. The sequence of any such control peptide is derived from the sequence of its functionally active counterpart by substituting a few amino acid residues in the parent amino acid sequence with other amino acid residues likely to produce a significantly different conformation (See, e.g. Carr et al., supra; and Rosenmund et al., *Nature* 368:853–856, 1994).

Microinjection of AIPs into neurons or skeletal muscle cells has been shown to disrupt PKA anchoring and PKA modulation of glutamate receptor channels (Rosenmund et al., supra) and voltage-gated calcium channels (Johnson et al., *Proc. Natl. Acad. Sci. USA* 91:11492–11496, 1994).

However, microinjection is impractical for normal pharmaceutical applications. If a more practical method were found for introducing AIPs and other functionally active peptides intracellularly, it would lead to many possible applications, particularly those applications involving the control and regulation of cyclic adenosine monophosphate (cAMP) mediated responses in living cells.

Cyclic AMP (cAMP) is known to mediate the motility of sperm and a variety of other ciliated cells (Satir, *Modern Cell Biol.* 4:1–46, 1985; Tash, *Cell Motil. Cytoskel.* 14:332–339, 1989; Bedford and Hoskins, in *Marshall's Physiology of Reproduction*, Lamming, ed., pp. 379, Churchill Livingstone, N.Y. 1990). Increases in the level of this nucleotide are associated with development of motility in the epididymis (Bedford and Hoskins, supra; Hoskins et al., *J. Reprod. Fertil.* 37:131–133, 1974). Cell-permeant cAMP analogs, e.g., cAMP phosphodiesterase inhibitors, and adenyl cyclase activators, all stimulate motility of sperm from several species (Garbers et al., *Biol. Reprod.* 7:132, 1972; Garbers et al., *Adv. Cyclic Nucleotide Res.* 9:583–595, 1978; Hoskins, *Journal of Biological Chemistry* 248:1135–1140, 1973; Hoskins et al., *Biol. Reprod.* 13:168–176, 1975; Vijayaraghavan and Hoskins, *J. Cyclic Nucleotide Protein Phosphoryl. Res.* 10:499–510, 1985). The kinetic and metabolic responses to cAMP elevation have been discovered to occur within 5 to 10 minutes (Garbers et al., *Biol. Reprod.* 7:132, 1972; Garbers et al., *Adv. Cyclic Nucleotide Res.* 9:583–595, 1978).

Sperm are known to lack nucleic-acid and protein-synthetic activity, thereby considerably reducing the possible range of targets of cAMP action. Sperm have been found to have distinct subcellular structures easily distinguished with the aid of a light microscope. Immunogold staining of sperm, followed by examination under a light microscope, has been used to demonstrate a predominant localization of the type II subunit (RII) of a PKA anchoring protein at the outer membrane of the mitochondria that spiral around the proximal flagella (Lieberman et al., *J. Cell Biol.* 107:1809–1816, 1988). A developmentally regulated sperm AKAP (i.e., AKAP-84) has also been localized to sperm mitochondria (Lin et al., *J. Biol. Chem.* 270:27804–27811, 1995).

Cyclic AMP and the proteins which regulate the production of cAMP in living cells, such as the various protein kinase regulatory anchoring proteins (e.g. AKAPs), are important in mediating many different responses in a wide variety of cells, other than the motility response in sperm cells. For example, AKAPs have been found to play a critical role in the regulation of synaptic function in cultured hippocampal neurons (Rosenmund et al., supra).

Therefore, what is needed is a product or process for introducing peptides known to be functionally active into the intracellular space of living cells. As used herein, the term "intracellular space" refers to the region of a cell bounded by the cell membrane or cell wall. In the case of a eukaryotic cell, the term intracellular space refers to everything contained within the cytoplasm of the cell, including all organelles and regions of proteins protruding into the cytoplasm from the inner surface of the cell membrane. Particularly needed is a product or process for introducing AIPs into the intracellular space of living cells and, more particularly, AIPs capable of inhibiting the binding of specific protein kinases to specific protein kinase anchor proteins. Disclosed herein is such a product, e.g., an alkyl peptide amide, and a process for the introduction of at least the amide portion of the product into the intracellular space of living cells.

Also disclosed herein are examples of the synthesis and use of such alkyl peptide amides to inhibit the activity of protein kinase A in HeLa cells and to inhibit binding between the RII subunit of protein kinase A and the anchor binding protein in sperm from various different organisms.

BRIEF SUMMARY OF THE INVENTION

The principal aspects of the invention are as follows. In one aspect the present invention is an alkyl peptide, comprising:

an alkyl moiety having at least twelve (12) carbon atoms;

a peptide moiety, the peptide moiety having an inhibitor region comprising a sequence of amino acids substantially homologous to a binding domain within a first protein, wherein the binding domain is capable of binding a second protein in the intracellular space of a living cell; and a linkage between the alkyl moiety and the peptide moiety.

In another aspect, the present invention is an alkyl peptide amide, comprising:

an alkyl moiety having at least twelve (12) carbon atoms, the alkyl moiety including a carbonyl terminus;

a peptide moiety, the peptide moiety having an inhibitor region and an N-terminus, the inhibitor region comprising a sequence of amino acids substantially homologous to a binding domain within a first protein, wherein the binding domain is capable of binding a second protein in the intracellular space of a living cell; and an amide linkage between the carbonyl terminus of the alkyl moiety, and the N-terminus of the peptide moiety.

In a further aspect, the present invention is a pharmaceutical composition comprising an alkyl peptide amide described above in a pharmaceutically acceptable carrier.

In yet a further aspect, the present invention is a method of using an alkyl peptide amide to inhibit the binding of a first protein to a second protein in a living cell, comprising the steps of:

(a) selecting a living cell having a first protein, a second protein, and a cell membrane surrounding an intracellular space, wherein the first protein has at least one binding domain capable of binding the second protein in the intracellular space;

(b) providing an alkyl peptide amide, comprising:
an alkyl moiety of at least twelve (12) carbon atoms, the alkyl moiety having a carbonyl terminus;
a peptide moiety, the peptide moiety having an inhibitor region and an N-terminus, the inhibitor region comprising a sequence of amino acids substantially homologous to the binding domain within the first protein for the second protein; and
an amide linkage between the carbonyl terminus of the alkyl moiety, and the N-terminus of the peptide moiety; and (c) exposing the alkyl peptide amide to the living cell so that the peptide moiety permeates the cell membrane and inhibits the binding of the first protein to the second protein.

The alkyl peptide amides of this invention are efficient delivery systems for introducing peptide moieties into the intracellular space of living cells, including sperm cells and HeLa cells. The motility of sperm cells from a wide variety of different species can be inhibited after such cells are exposed to the alkyl peptide amide form of AIPs (i.e. alkyl AIP amides). This last form of the alkyl peptide amides of this invention (alkyl AIP amides) can be included in pharmaceutical compositions and used as contraceptives, either alone or in combination with other contraceptive substances, e.g., a spermicidal agent such as nonoxynol-9.

The pharmaceutical compositions of the alkyl peptide amides of this invention include pharmaceutical contraceptive compositions, particularly such compositions comprising an alkyl peptide amide known to inhibit sperm motility, such an alkyl AIP amide. The pharmaceutical contraceptive compositions of this invention can be used in the form of a topical ointment or lotion e.g., to lubricate the vagina before intercourse. Other modes of application of the pharmaceutical composition of the invention are likely to occur to one skilled in the contraceptive art. By inhibiting sperm motility, the contraceptive compositions of this invention could prevent fertilization of the ovum (alone or in combination with other contraception techniques), with minimal side effects.

The pharmaceutical contraceptive compositions of this invention are likely to produce few side effects because: (1) the peptide moiety of the alkyl peptide amide has a substantially similar sequence to a natural cellular component; (2) only very low concentrations of the alkyl peptide amide component are needed for a composition to be effective as an inhibitor of sperm motility; and (3) the effect, i.e., sperm motility inhibition, has been found to be temporary, i.e., to be reversible once sperm cells are no longer in contact with a composition containing the alkyl peptide amide.

The detailed disclosure below demonstrates that the compositions and methods of the present invention can be used to introduce inhibitor moieties, such as peptide or peptidomimetic moieties into the intracellular space of a variety of different types of cells, including sperm cells obtained from various different species, and HeLa cells (a continuously cultured cell line, originally obtained from human cancerous cervical tissue.) Aspects of this invention may also have utility in other applications which will occur to one skilled in this art in light of the disclosure herein. One such aspect is the inhibition of transformation in certain tumorous cells. All such other applications are included within the scope of this invention.

BRIEF DESCRIPTION OF THE DRAWING(S)

FIG. 1 Schematic diagram showing the disruption of binding between a pair of cAMP dependent regulatory subunit proteins and a membrane bound anchoring protein by an alkyl AIP amide in the intracellular space of a living cell.

Figure 2:
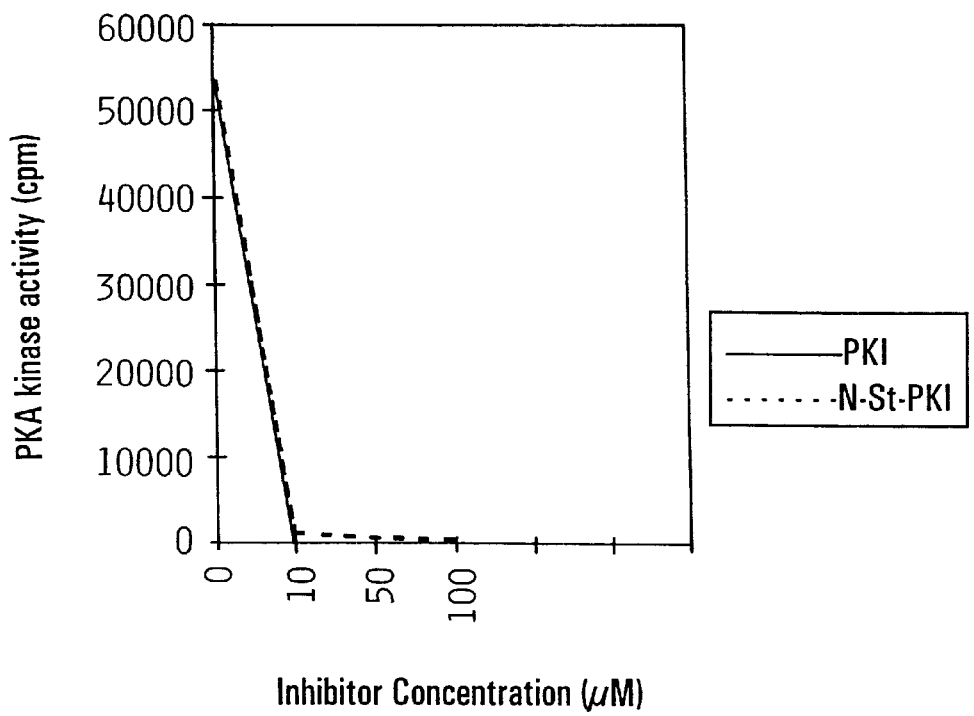

FIG. 2 Plot of PKA Kinase activity versus inhibitor concentration obtained from processing and assaying HeLa cells after treatment with PKI or with s-PKI (N-ST-PKI).

Figure 3:
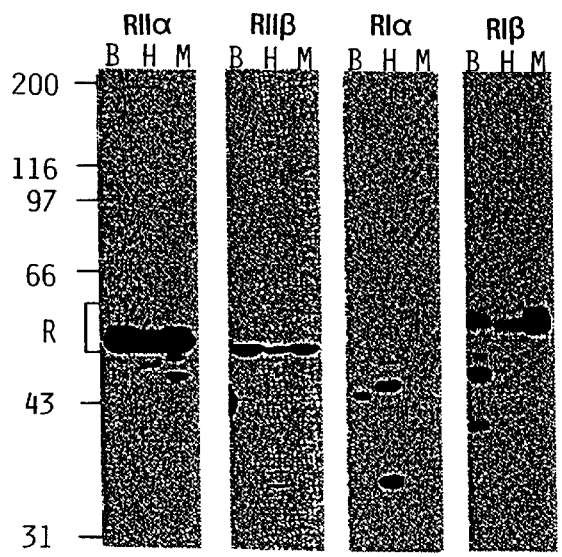

FIG. 3 Autoradiograms of Western blots of sodium D-lauroyl sulfate (SDS) polyacrylamide gel electrophoresis (PAGE) of $^{32}$P-labeled cAMP-dependent protein kinase A subunits, RIα, RIβ, RIIα, and RIIβ of sperm extracts from bovine (B), human (H), and monkey (M).

Figure 4:
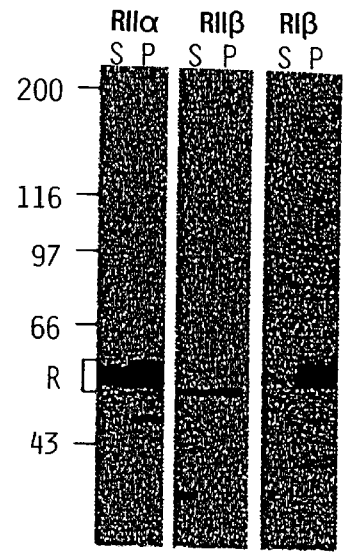

FIG. 4 Autoradiograms of Western blot/SDS-PAGE of bovine caudal epididymal sperm lysed and separated into supernatant (S) and pellet (P) fractions by centrifugation,and probed using anti-RIIα, anti-RIIβ, and anti-RIβ antibodies.

Figure 5:
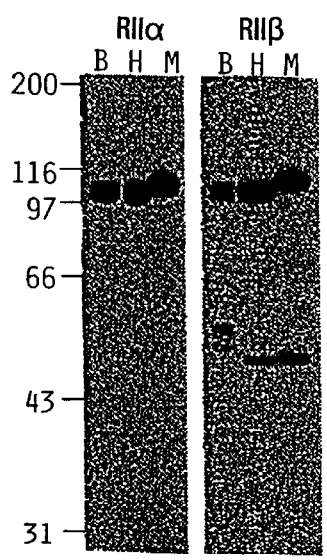

FIG. 5 Autoradiograms of Western blot/SDS-PAGE of sperm extract from bovine, human, and monkey probed with $^{32}$P-labeled RIIα or RIIβ.

Figure 6:
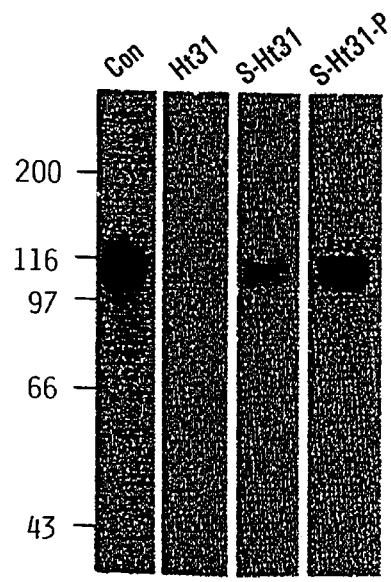

FIG. 6 Autoradiograms of Western blot/SDS-PAGE showing the disruption of RII binding to bovine sperm AKAP in the presence or absence of 20 μM of the anchor inhibiting peptide Ht31, 20 μM of a stearyl peptide amide form of Ht31 (s-Ht31), or 20 μM of a stearyl peptide amide form of an Ht31 control peptide (s-Ht31-P).

Figure 7:
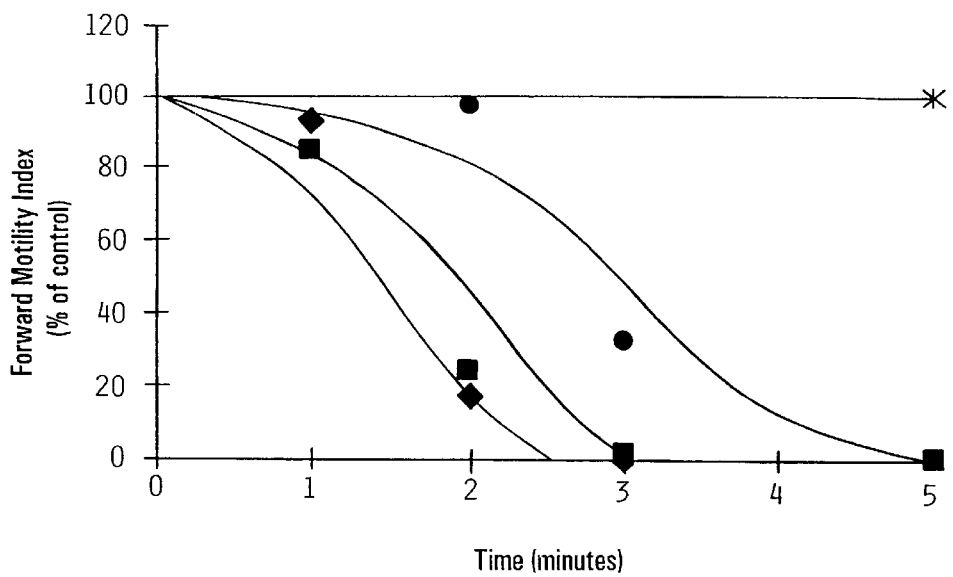

FIG. 7 Plot of forward motility as a percentage of control versus incubation time, obtained from testing bovine sperm after incubation for varying amounts of time in a buffer containing 50 μM s-Ht31-P (control) (x), or 5 μM (●), 10 μM (■), or 50 μM (♦) of s-Ht31.

Figure 8:
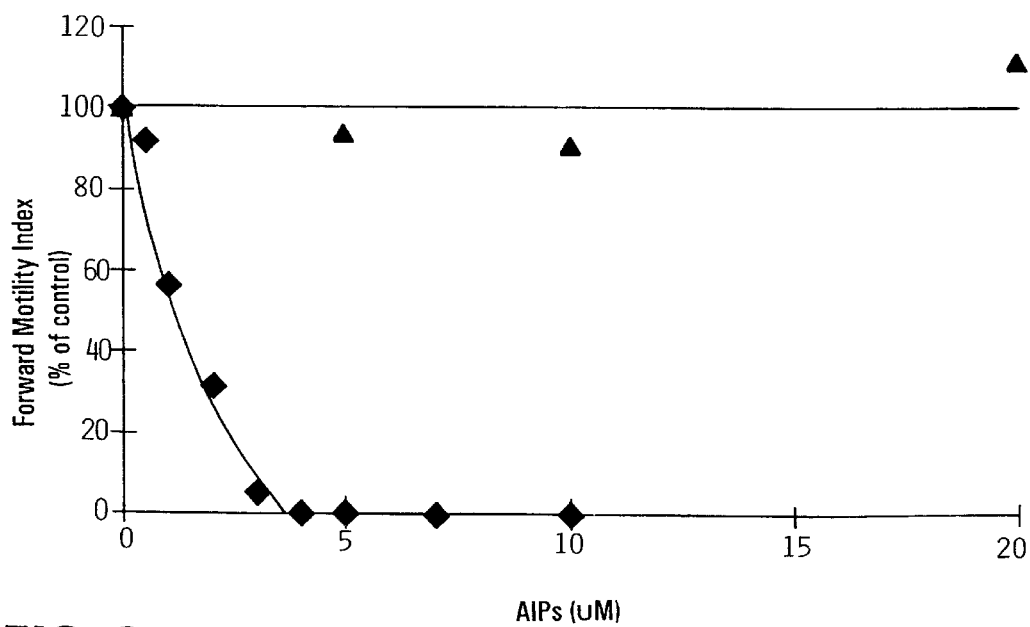

FIG. 8 Plot of forward motility as a percentage of control versus concentration of stearyl peptide amides (derivatives of AIPs), obtained from testing bovine sperm after 5 minutes of incubation in a buffer, after adding varying amounts of s-Ht31 (♦) or s-Ht31-P control (▲).

Figure 9:
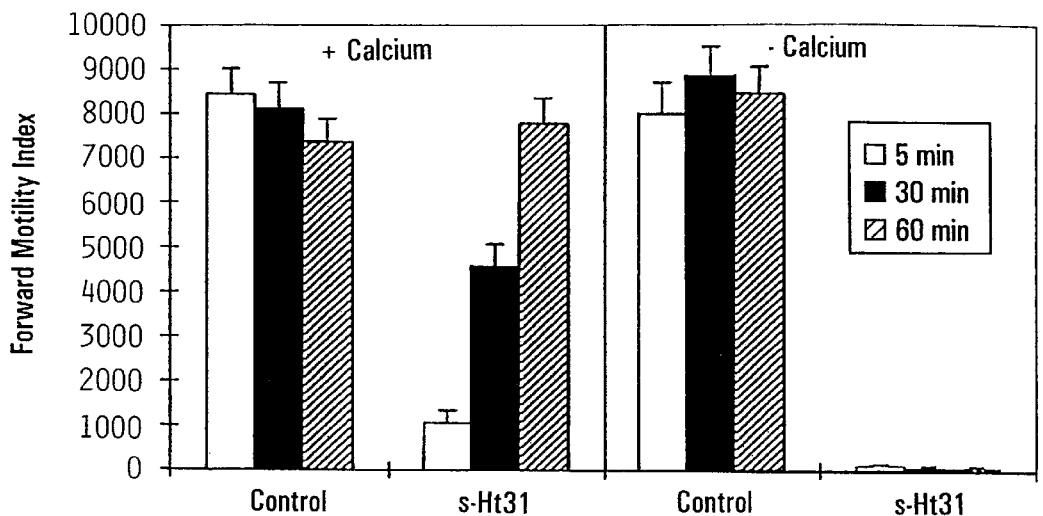

FIG. 9 Histogram of forward motility index obtained from bovine caudal epididymal sperm after treatment with water (control) or 10 μM s-Ht31 and recovery for varying amounts of time in a buffer containing 2 mM calcium (+Calcium) or 2 mM EGTA (−Calcium).

Figure 10:
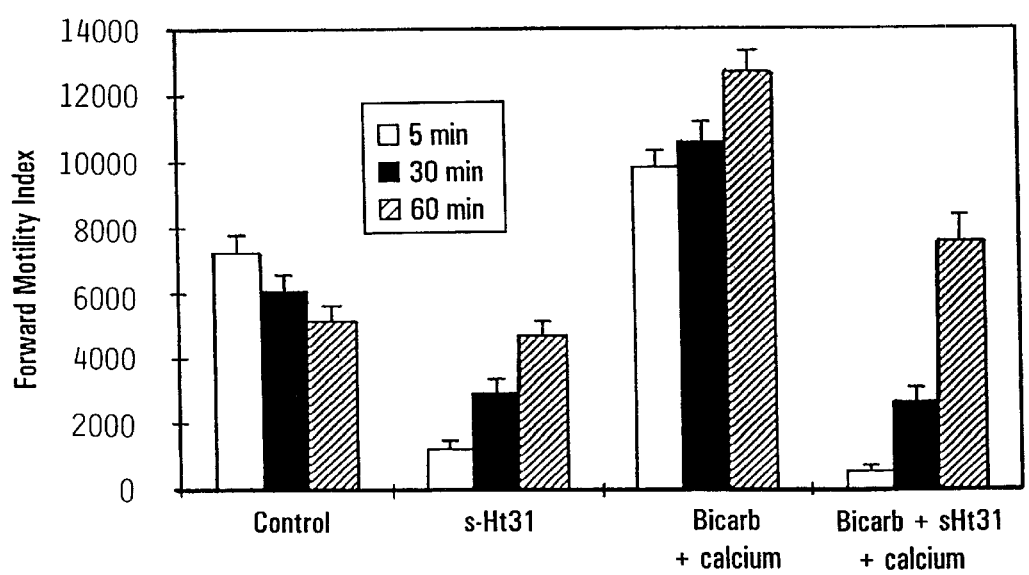

FIG. 10 Histogram of forward motility index of bovine caudal epididymal sperm after treatment with water (control) or 10 μM s-Ht31 and recovery for varying amounts of time in a buffer with or without 2 mM calcium and 50 mM bicarbonate.

Figure 11:
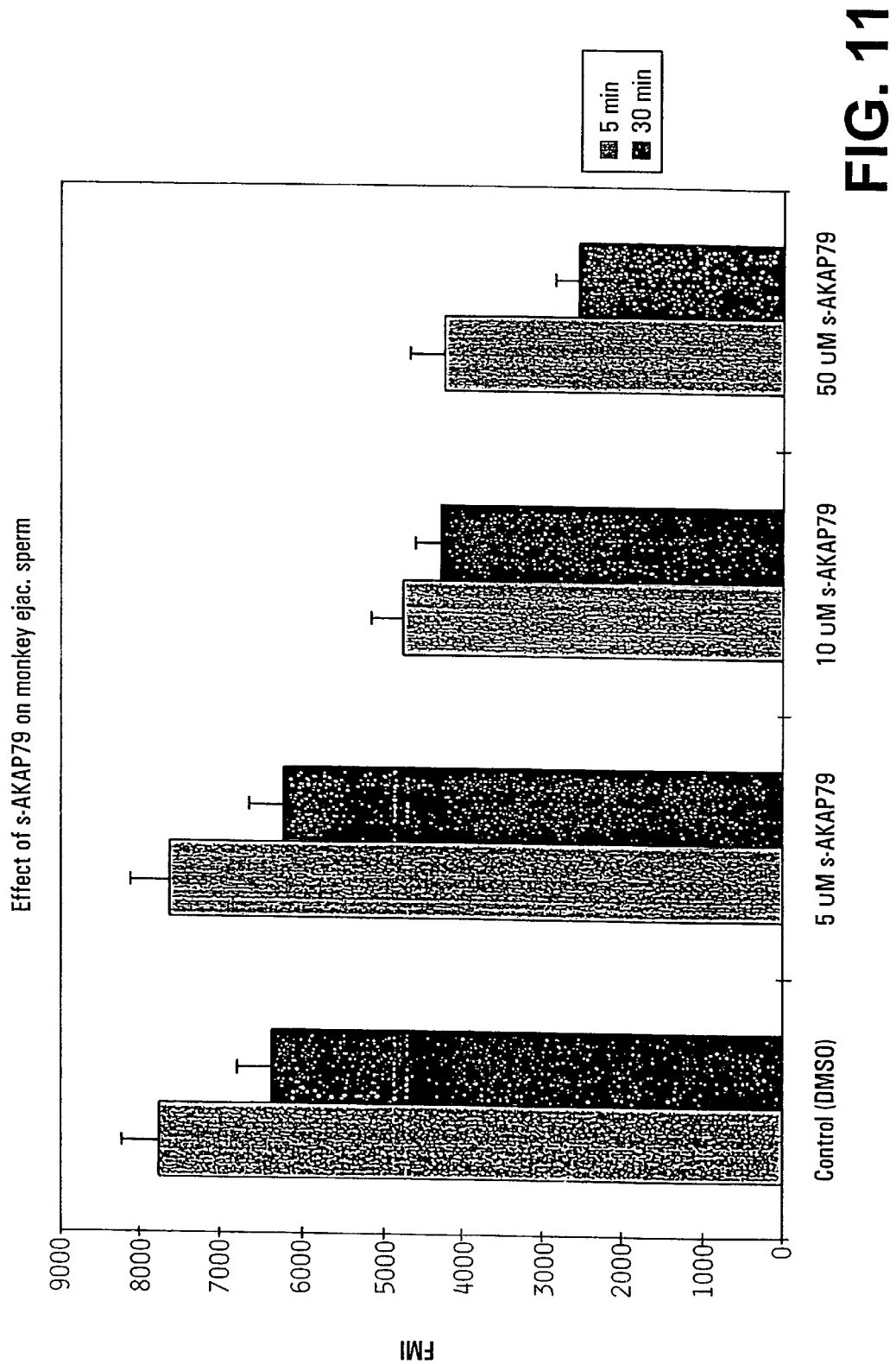

FIG. 11 Histogram of forward motility index of monkey ejaculated sperm after incubation for 5 or 30 minutes in a buffer containing dimethyl sulfoxide (DMSO) (control) and varying amounts of the stearyl AIP amide s-AKAP79.

Figure 12:
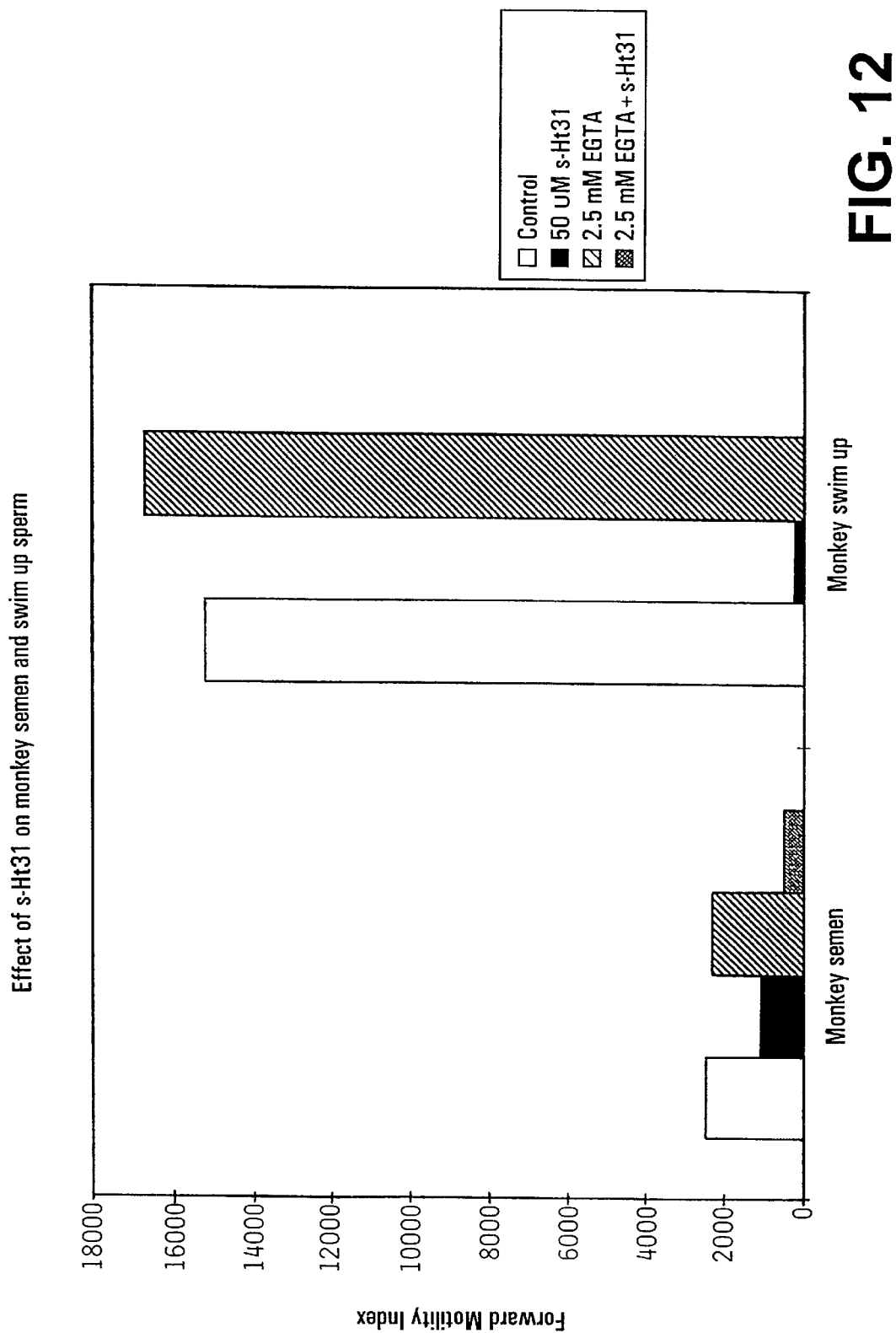

FIG. 12 Histogram of forward motility index of monkey sperm from neat semen or semen collected after swim-up analysis, after incubation for 15 minutes after no addition (control), or after addition of 100 μM s-Ht31, 2.5 mM EGTA, or 2.5 mM EGTA plus 50 μM s-Ht31.

Figure 13:
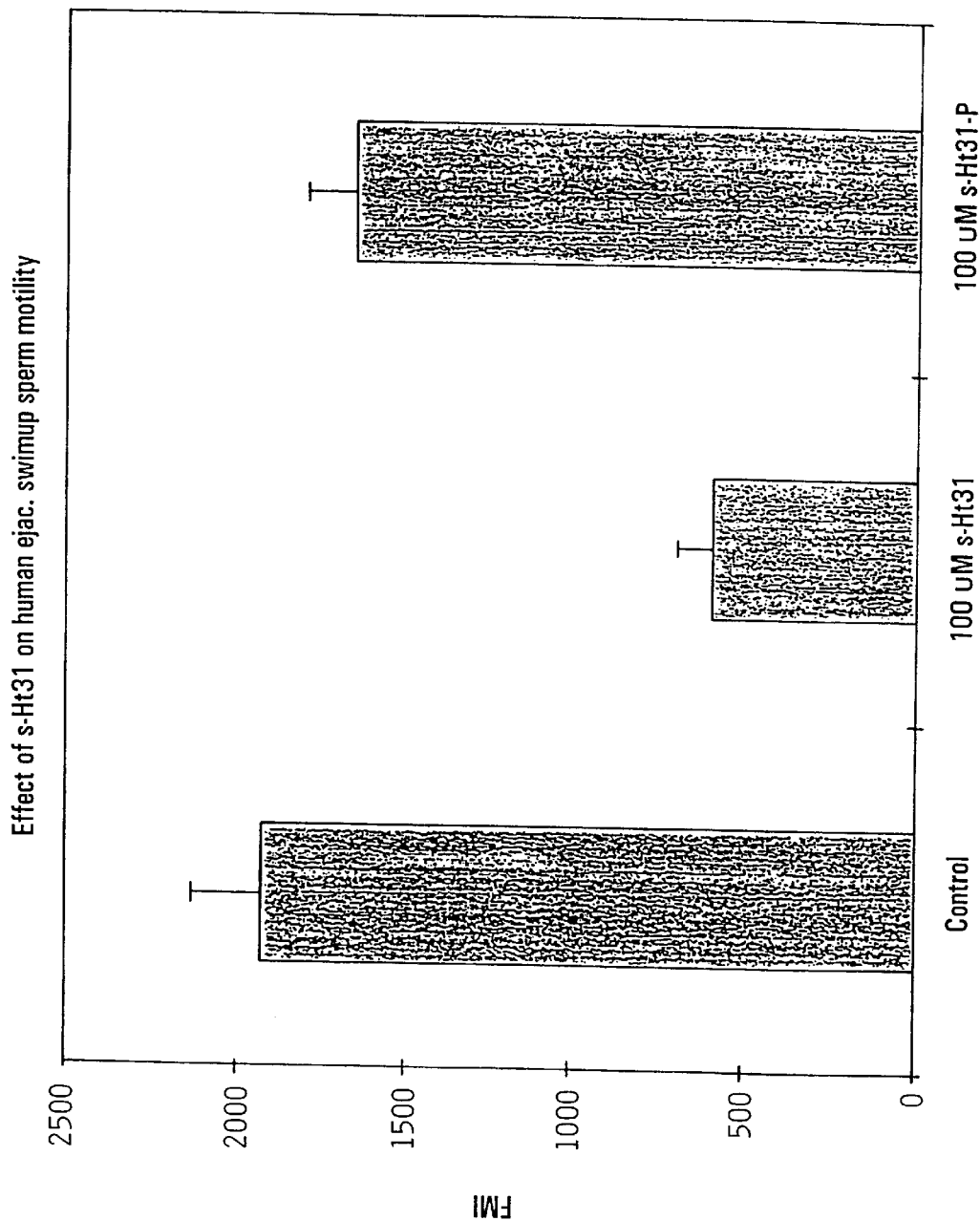

FIG. 13 Histogram of forward motility index of human ejaculated sperm after swim-up analysis, after incubation for 15 minutes after no addition (control), or after addition of 100 μM s-Ht31 or s-Ht31-P.

Figure 14:
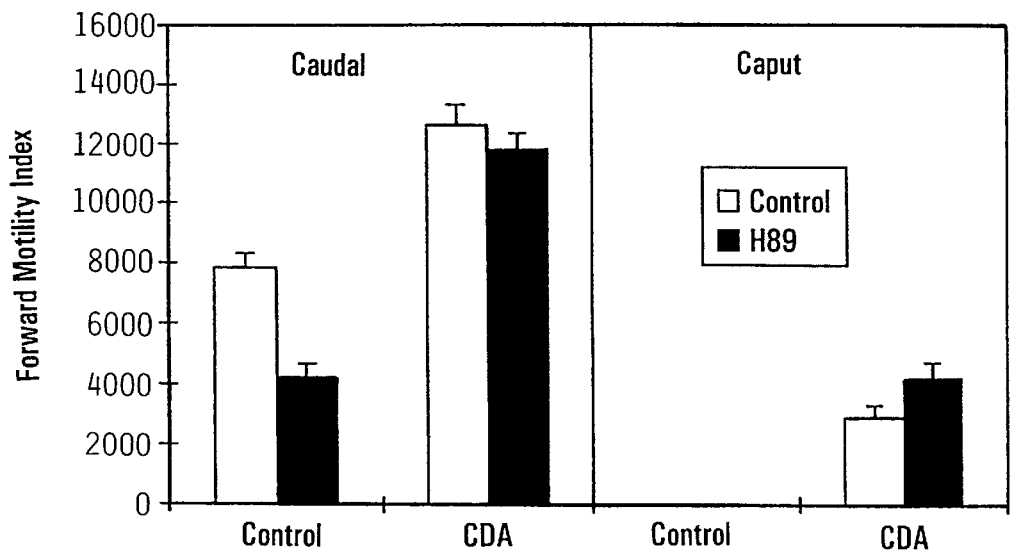

FIG. 14 Histogram of forward motility index of bovine caudal and caput sperm, after incubation for 15 minutes in the presence or absence of 50 μM 2-chloro-2'-deoxyadenosine (CDA) and/or 50 μM of the protein kinase inhibitor H-89.

Figure 15:
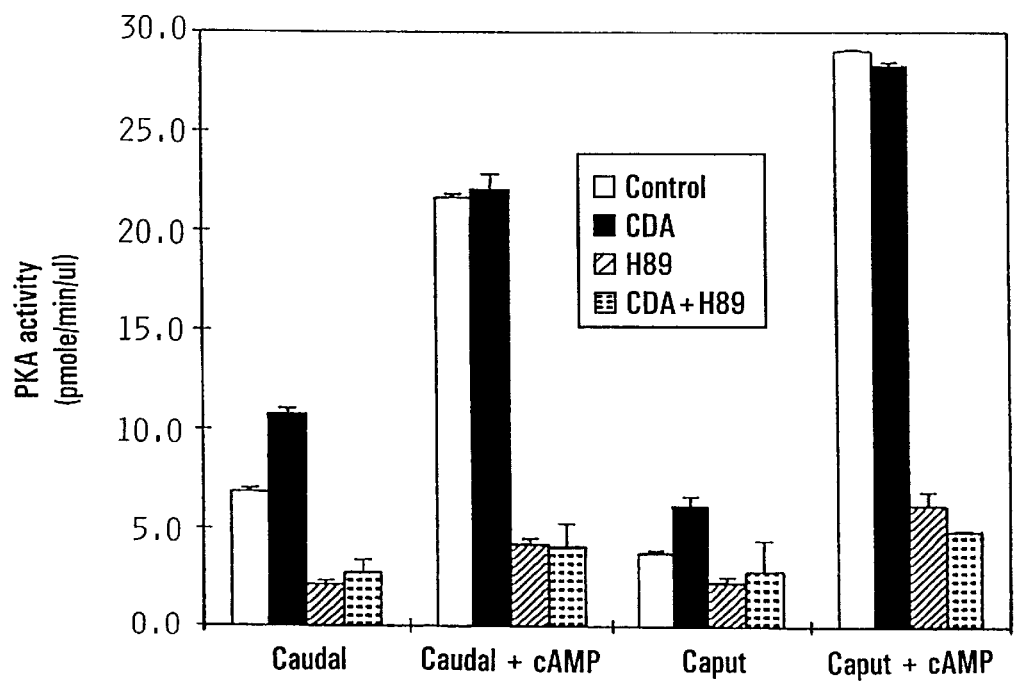

FIG. 15 Histogram of PKA kinase activity of bovine caudal and caput sperm, after incubation as described in FIG. 12 followed by an assay for PKA activity.

Figure 16:
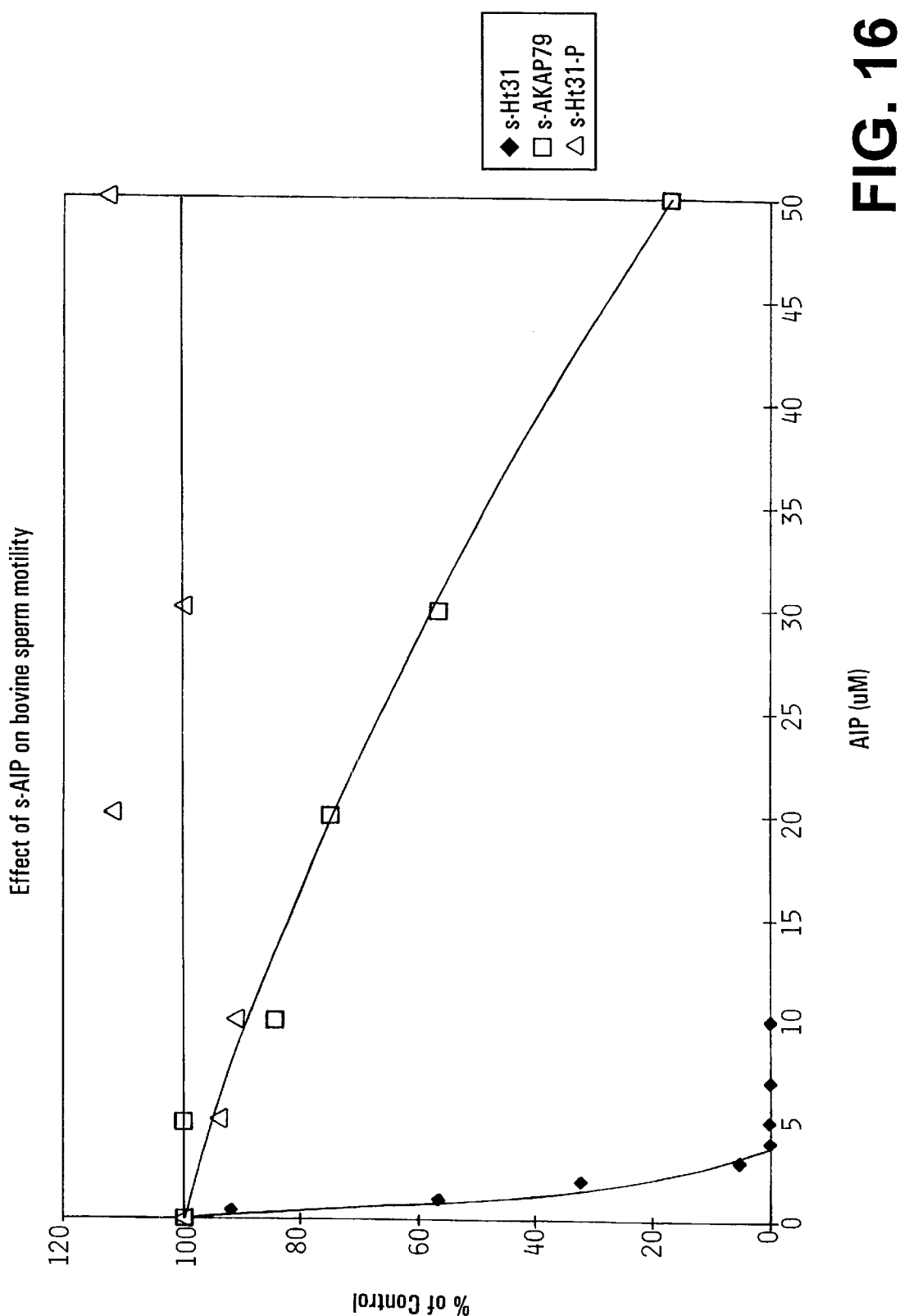

FIG. 16 Plot of forward motility as a percentage of control, obtained from bovine sperm incubated for 5 minutes in a buffer containing increasing amounts of s-Ht31 (♦), s-AKAP79 (□), or s-Ht31-P (control) (Δ).

DETAILED DESCRIPTION OF THE INVENTION

The alkyl peptide of this invention comprises an alkyl moiety linked to a peptide moiety or to a peptidometric moiety. A peptidomimetic moiety consists of a moiety produced from at least one organic molecule other than a peptide, which mimics the biological activity of a peptide moiety of an alkyl peptide. The alkyl peptide of this invention is preferably an alkyl peptide amide, more preferably an alkyl peptide amide comprising an alkyl moiety and a peptide moiety linked by an amide bond between a terminal nitrogen residue of the peptide moiety (an N-terminus) and the terminal carbonyl residue of the alkyl moiety (carbonyl terminus). The alkyl moiety comprises a saturated, straight chain of at least 12 carbon atoms (including the carbonyl terminus), or a chain of at least 12 carbon atoms optionally substituted by at least one other component such as a halogen, or a lower alkyl group having from one to six carbon atoms and especially a very short alkyl group such as a methyl or ethyl group. The alkyl moiety is preferably a saturated, straight chain of at least 14 carbon atoms and most preferably a stearyl group (i.e. a straight 17 carbon atom chain having a carbonyl terminus).

Herein below is a detailed description of the alkyl peptide amide aspect of the present application. However, the detailed description below is not intended to limit the invention to that particular embodiment of the invention.

In addition to an N-terminus, the peptide moiety also includes an inhibitor region, comprising a sequence of amino acids substantially homologous to a sequence of amino acids in a binding domain of a specific protein (a first protein), a binding domain capable of binding a particular protein of interest (a second protein) in the intracellular space of a living cell. The sequence of amino acids in the inhibitor region of the peptide moiety is preferably substantially homologous to a sequence of amino acids in the binding domain of a first protein capable of binding a protein kinase in the intracellular space of a living cell; more preferably a binding domain capable of binding PKA. In one preferred aspect of the alkyl peptide amide of this invention the inhibitor region of the peptide boiety consists of an amino acid sequence substantially homologous to the sequence of amino acids in a binding domain of a first protein, wherein the first protein is an anchoring protein, more preferably a binding domain of AKAP which is known to, or suspected of, binding to the regulatory subunit of PKA.

The inhibitor region of the peptide moiety must be of a sufficient length to inhibit the binding of a second protein to the binding domain of a first protein, wherein the sequence of amino acids in the inhibitor region of the moiety is substantially homologous to the binding domain of the first protein. The length of the entire peptide moiety is most preferably sufficient for the moiety to pass into the intracellular space of a living cell with the inhibitor region of the moiety sufficiently intact to disrupt binding between a second protein and a first protein. The minimum length of the entire peptide moiety component of the alkyl peptide amides of this invention is preferably about 4 amino acid residues, more preferably about 10 amino acid residues, and most preferably about 20 amino acid residues. The maximum length of the entire peptide moiety is preferably less than about 40 amino acid residues, more preferably less than about 30 amino acid residues, and most preferably less than about 25 amino acid residues.

The peptide used to produce the alkyl peptide moiety can be synthesized using any standard peptide synthesis method, preferably using an automated peptide synthesizer, more preferably using an automated peptide synthesizer using 9-fluorenylmethoxycarbonyl (FMOC) chemistry employing base-mediated coupling. The polypeptide can also be purified before use in making the alkyl peptide amide of the invention, using any suitable means for purifying a polypeptide known in the art (Shaw, C., *Methods in Molecular Biology* 32:275–287 1994).

The carbonyl terminus of the alkyl moiety is linked to the N-terminus of the peptide moiety to form the alkyl peptide amide of the invention. The link is preferably formed, through a base-catalyzed nucleophilic addition, by reacting the carboxylic acid terminus of a fatty acid, such as stearic acid, with the N-terminus of a peptide having an inhibitor region, under reaction conditions designed to protect the peptide from degradation. Formally, the reaction may be written as follows:

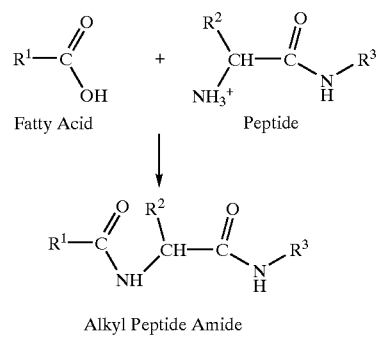

Alkyl Peptide Amide wherein $R^1$ is a saturated chain of at least 11 carbon atoms, optionally substituted by at least one component such as a halogen or a lower alkyl group, as described above; wherein $R^2$ is an amino acid R group (see e.g. description of amino acid R groups in A. L. Lehninger, *Principals of Biochemistry*, Worth Publishers, Inc., 1982, p. 101); and wherein $R^3$ is a peptide chain of at least four amino acid residues, terminating in a carboxyl group (i.e. the C-terminus of the peptide moiety).

The peptide is preferably protected during the reaction described above by being covalently linked to at least one substantially inert protection group prior to being exposed to the fatty acid. The fatty acid is preferably activated before being exposed to the peptide. The link between the fatty acid and the peptide is preferably formed in the presence of an activator using diiosopropylethylamine, an activator such as benzotriazole-1-yl-oxy-tris(dimethylamino)phosphoniumhexafluorophosphate (BOP) or O—(7-azabenzotriazole-1-yl)-1,1,3,3,-tetramethyluroniumhexafluorophosphate (HATU).

Formation of the alkyl peptide amide in the reaction described above can be monitored using any one of a number of different monitoring methods, including staining samples of the reaction mixture with ninhydrin (an amino acid selective blue stain), or cleaving the resulting products with trifluoroacetic acid (TFA). Monitoring is preferably done using a combination of mass spectrometry and high performance (or high pressure) liquid chromatography (HPLC).

The alkyl peptide amide product of the peptide/fatty acid linkage reaction described above is preferably isolated from other components of the reaction solution, preferably by HPLC, and more preferably by reverse phase HPLC using a C8 column employing a TFA/acetonitrile buffer system. If HPLC is used to purify the alkyl peptide amide, the eluent is preferably analyzed to identify the fractions of eluent containing the alkyl peptide amide, preferably using mass spectrometry, more preferably using a time of flight (TOF) mass spectrometry analyzer. Fractions containing the largest amounts of alkyl peptide amide are then preferably pooled, and analyzed again to confirm the purity of the final alkyl peptide amide product.

Alkyl peptide amides synthesized and isolated according to the preferred procedures described above can be stored in a stabilizing buffer at room temperature or colder, but are more preferably stored in lyophilized form, even more preferably in lyophilized form under nitrogen.

The alkyl peptide amides of this invention are designed to introduce the peptide moiety into the intracellular space of a living cell, where it can disrupt or inhibit binding between one or more first proteins and one or more second proteins. The capacity of a given alkyl peptide amide to disrupt or inhibit binding between a first protein and a second protein often depends upon how similar the sequence of the inhibitor region of the peptide moiety is to the sequence of amino acids in the binding domain of the first protein, wherein the binding domain is capable of binding the second protein in the intracellular space of a living cell. In a preferred aspect, the sequence of amino acids in the inhibitor region of the peptide moiety of the alkyl peptide amide is preferably substantially homologous to the amino acid sequence of the binding domain of the first protein, more preferably substantially homologous to a binding domain capable of binding to a protein kinase in the intracellular space of a cell, most preferably substantially homologous to a sequence of amino acids in the PKA binding domain of an anchoring protein, such as in the PKA binding domain of AKAP. Peptides containing sequences of this last most preferred type are commonly known as AIPs. This particular preferred embodiment of the alkyl peptide amides of the present invention is referred to herein as alkyl AIP amides.

It is contemplated that nonhomologous peptides or other organic molecules such as peptidomimetics that have structural identity that is sufficient to disrupt the interaction between AKAPS and PKA could be substituted for the peptide moiety of alkyl AIP amides described herein, and similarly be used to inhibit sperm motility and other AKAP-anchored, PKA-medicated responses.

FIG. 1 is a schematic diagram showing the interaction of an alkyl AIP amide with a membrane-bound anchoring protein to inhibit binding between the anchoring protein and a regulatory subunit homodimer of PKA. In the absence of such a binding inhibitor, cAMP generating enzymes such as adenylate cyclase (a membrane associated enzyme) can be activated by ligands (hormones, neurotransmitters, etc.) or by activators (forskolin or cAMP analogues). The activated adenylate cyclase converts ATP to the second messenger cAMP. The second messenger cAMP, in turn, interacts with PKA, causing the regulatory subunit homodimer to dissociate from the catalytic subunit of PKA. The regulatory subunits are then translocated to the membrane where they attach to the anchoring protein. By inhibiting or disrupting binding between the regulatory subunits of PKA and the anchoring protein, the alkyl AIP amides of this invention inhibit the physiological functions mediated by the interaction of an anchoring protein with the regulatory subunits.

FIG. 1 is merely illustrative of one possible mode of action of one embodiment of the alkyl peptide amides of this invention. This invention is not limited by any theory or any postulated mode of action. Thus neither the schematic diagram of FIG. 1 nor its description immediately above are intended to limit the scope of the invention.

The present invention is not limited to the alkyl peptide or alkyl peptide amide aspects described in general terms above, and in greater detail through the definitions and examples below. The present invention encompasses any alkyl inhibitor amide comprising an alkyl moiety linked to an inhibitor moiety through an amide bond, wherein the inhibitor moiety comprises an inhibitor region capable of inhibiting or disrupting binding between a first protein and a second protein in the intracellular space of a living cell. The inhibitor moiety is preferably a peptide moiety or a peptidomimetic moiety, wherein the peptidomimetic moiety consists of a moiety produced from at least one organic molecule other than a peptide, which mimics the biological activity of a peptide inhibitor moiety.

The inhibitor region of a peptide inhibitor moiety consists of a sequence of amino acid residues which is capable of inhibiting or disrupting binding between a first protein and a second protein in the intracellular space of a living cell. The sequence of amino acid residues in the inhibitory region of such a peptide moiety can be selected by sythesizing and testing a series of peptides with random sequences until a sequence is identified which produces the targeted inhibitory effect. When such a screening method is used, the resulting inhibitory region sequence will not necessarily be substantially homologous to the binding domain of either the first or the second protein. In the most preferred aspect, however, the sequence of amino acids in the inhibitor region of the alkyl peptide amide of the present invention is substantially homologous to at least one sequence of amino acid residues in the binding domain of a first protein which is capable of binding a second protein in the intracellular space of a living cell.

The alkyl peptidomimetic amides of the present invention are preferably produced by forming an amide bond linking the carboxyl residue at the carboxyiic acid terminus of a fatty acid molecule to the amine residue at a terminus of a peptidomimetic moiety precurser. The composition of the inhibitor region of the peptidomimetic moiety is selected to mimic the inhibitory or disruptive functionality of the inhibitory region of an peptide moiety of an alkyl peptide amide of this invention. The inhibitory functionality of an alkyl peptidomimetic amide of the present invention is preferably similar to that of an alkyl peptide amide, more preferably at least as high as that of an alkyl peptide amide, and most preferably greater than that of an alkyl peptide amide. Methods for producing peptidomimetic molecules with such inhibitory potencies are known. (See, e.g. Eichler et al., Med. Res. Rev., 15: 481–496, 1995, incorporated by reference herein.).

The peptide moiety of the alkyl inhibitor amide can be produced by forming an amide bond with an amine group at either terminus of a peptide molecule. Normally, a peptide molecule contains only one N-terminus. However, the carboxylic acid residue (i.e. the C-terminus) of a peptide molecule can be modified by substituting an amine group for the hydroxyl group at that terminus, thereby producing a second N-terminus.

Definitions and Details of Preferred Embodiments

The following definitions and additional details of the preferred embodiments of the invention are provided to guide those of ordinary skill in the art in understanding and making and using the compositions of this invention. Definitions of common terms used here may also be found in Rieger et al., *Glossary of Genetics: Classical and Molecular*, 5th edition, Springer-Verlag: New York, 1991; and Lewin, *Genes V*, Oxford University Press: New York, 1994. The standard one-letter nomenclature for amino acid residues is used herein. "Anchoring Inhibiting Peptides". An anchoring inhibiting peptide or AIP is defined as a peptide that (1) is at least 4 amino acids in length; (2) possesses an amphipathic α-helical structure; (3) binds to PKA; and (4) interferes with binding of PKA to an AKAP.

Subcellular localization of PKA is directed through the regulatory (R) subunit. There are two R subunit classes, RI and RII, which form the type I and type II holoenzymes, respectively. Type II PKA is present in all eukaryotic cells, whereas the tissue distribution of type I PKA is more restricted. Type II PKA localization is dictated by the association of RII with AKAPs. Tissue-specific AKAP localization has been detected by protein-blotting techniques or by fractionation on RII-Sepharose affinity columns.

All AKAPs identified to date contain an amphipathic helix domain that is responsible for RII binding (Carr et al., *J.*

Biol. Chem. 266:14188–14192, 1991; Carr et al., *J. Biol. Chem.* 267:13376–13382, 1992; Carr et al., *J. Biol. Chem.* 267:16816–16823, 1992; Coghlan et al., *J. Biol. Chem.* 269:7658–7665, 1994; McCartney et al., *J. Biol. Chem.* 270:9327–9333, 1995).

"Amphipathic Helix." An amphipathic helix is an α-helix with opposing hydrophilic and hydrophobic faces oriented down the long axis of the helix. As discussed in Example 3 below, substantial disruption of the α-helical structure of a functionally active peptide, such as an AIP, significantly reduces or eliminates functional activity, such as the binding of an AIP to RII.

The RII-binding amphipathic helix of an AKAP can be identified by a computer-aided secondary structure prediction method (Eisenberg et al., *Proc. Natl. Acad. Sci. USA* 81:140–144, 1984). A characteristic of the amphipathic helix motif of about 14 amino-acid residues is the ordered placement of alternating pairs of hydrophobic and hydrophilic amino acids within the linear sequence of a protein. In addition, each RII-anchoring protein contains acidic amino acids distributed over the hydrophilic face of the helix. In particular, a glutamic acid residue at position-3 is located within the first turn of the amphipathic helix of most wild-type AKAPS.

The same computer-aided secondary structure prediction method (or a combination of that method and a library screening approach), could also be employed to identify amphipathic helix motifs in the regions of AKAPs and other first proteins suspected to bind specific second proteins. The sequence of amino acids in the identified motifs could then be employed to obtain peptides with equivalent disrupting potency to the specific AIP sequences identified herein below.

Preferably, the AIP includes an amino acid sequence that is substantially identical to, or more preferably identical to that of the RII-binding portion of a "native" (naturally-occurring or wild-type) AKAP. Additional amino-acid residues may be included, preferably at the amino-terminus or carboxyl-terminus of the AIP, so as not to interfere with binding of the AIP to PKA.

Amphipathic helix sequences predicted to bind RII include, but are not limited to the sequences listed on Table 1, below:

TABLE 1

| Name | AKAP Amino Acid Residues | Amino Acid Sequence |
|---|---|---|
| Ht 31 | 494–507 | LIEEAASRIVDAVI (SEQ ID NO: 3) |
| MAP2 | 87–100 | TAEEVSARIVQVVT (SEQ ID NO: 4) |
| AKAP 150 | 429–442 | LIETASSLVKNAIE (SEQ ID NO: 5) |
| AKAP 79 | 392–405 | LIETASSLVKNAIQ (SEQ ID NO: 6) |
| AKAP 95 | 642–659 | EVAAEVLAEVITAAVKAV (SEQ ID NO: 7) |
| AKAP 100 | 396–411 | IIDMASTALKSKSQ (SEQ ID NO: 8) |
| AKAP 220 | 905–918 | LAEKIVAEAIEKAE (SEQ ID NO: 9) |
| AKAP 84 | 355–376 | VISEATEQVLATTVGKVAGRVC (SEQ ID NO: 10) |

(Carr et al., *J. Biol. Chem.* 266:14188–14192, 1991; Carr et al., *J. Biol. Chem.* 267:13376–13382, 1992; Carr et al., *J. Biol. Chem.* 267:16816–16823, 1992; Coghlan et al., *J. Biol. Chem.* 269:7658–7665, 1994; McCartney et al., *J. Biol. Chem.* 270:9327–9333, 1995; Carr et al., *J. Biol. Chem.* 267:13376–13382, 1992). Any of the sequences listed immediately above are suitable for incorporation into the alkyl moiety of an alkyl peptide amide of this invention.

The sequence of the RII-binding domain of a wild-type AKAP polypeptide, i.e., a "native" AIP sequence, can be modified by substituting a hydrophobic amino-acid residue with another hydrophobic residue or substituting a hydrophilic residue with another hydrophilic residue, for example. Preferably acidic residues are replaced with other acidic residues. Residues that lie outside the predicted amphipathic helix region of an RII-binding region of an AKAP may enhance RII binding by stabilizing the overall conformation of the region and are preferably included in the AIP sequence. As a result, AIPs and alkyl AIP amides that include additional sequences from the RII-binding region of an AKAP flanking the helix-forming sequence are preferred. AIPs shorter than 14 amino-acid residues may also bind RII.

Suitable AIP sequences can also be identified by screening peptides for binding to RII. Random peptide sequences of at least about 14-amino acid residues that would be expected to form amphipathic helices can be identified by computer analysis. Alternatively, such sequences can be identified by screening for binding to PKA regulatory subunits using conventional methods including, but not limited to, combinatorial chemistry and expression library approaches (e.g., phage expression libraries, including those in which a peptide is joined in reading frame to an outer structural protein of the phage). The Examples below and Carr et al. (*J. Biol. Chem.* 266:14188–14192, 1991), discuss various assays, e.g., an RII gel overlay procedure, that are useful for screening phage expression libraries for polypeptides that bind to RII.

The AIPs used to make the preferred alkyl AIP amides of this invention are produced by standard synthesis techniques, preferably by chemical synthesis (see, e.g., Merrifield, *J. Amer. Chem. Soc.* 85:2149–2156, 1963). Alternatively, the AIPs can also be produced by standard genetic engineering techniques, i.e., by the expression of an AIP-encoding nucleic acid sequence in an appropriate host cell. The AIP may be expressed as a fusion polypeptide if binding to PKA is not significantly diminished by the fusion partner. For guidance regarding expression of polypeptides in various host cells, see, e.g., *Molecular Cloning: A Laboratory Manual*, 2nd ed., vol. 1–3, ed. Sambrook et al., Cold Spring Harbor Laboratory Press, Cold Spring Harbor, N.Y. 1989, and *Current Protocols in Molecular Biology*, ed. Ausubel et al., Greene Publishing and Wiley-Interscience, New York, 1987 (with periodic updates).

Alkyl AIP amides are capable of permeating cell membranes, and of introducing the AIP peptide moieties into the intracellular space of a living cells, where they can competitively disrupt the binding of PKA to AKAPs and cause loss of PKA modulation of cellular responses. Some of the alkyl AIP amides of this invention also inhibit sperm motility in a time- and concentration-dependent manner, when introduced to sperm in the form of an alkyl AIP amide. The inhibition of sperm motility by such an alkyl AIP amide (e.g., s-Ht31) is reversible, but only if calcium is present in the suspension buffer. Most spermicidal agents in current use employ non-specific toxic compounds (e.g., nonoxynol-9) that have adverse effects on cells lining the vaginal tract. Compositions of the alkyl AIP peptides of this invention are expected to have minimal side effects at concentrations that fully inhibit sperm motility.

Peptide Sequence Homology. Preferably, the inhibitor region of the peptide moiety of each of the alkyl AIP amides of this invention is at least about 70% homologous to a native AKAP-derived polypeptide, preferably at least about 80% homologous, and more preferably at least about 95% homologous. The inhibitor region of any of the alkyl peptide amides of this invention is said to be "substantially homologous" to the region of a first protein capable of binding a second protein if the alkyl peptide amide has an equivalent capacity to disrupt such binding, compared to an alkyl peptide amide having an inhibitor region which is homologous to the same region of the same first protein. The most preferred embodiments of the alkyl peptide amides of this invention, including the alkyl AIP amides, have such "substantial homology" or otherwise exhibit sufficient disruption or binding inhibition capability.

Peptide homology is typically analyzed using sequence analysis software such as the Sequence Analysis Software Package available from the Genetics Computer Group, University of Wisconsin Biotechnology Center, Madison, Wis).

"Isolated," "Purified," "Homogeneous" Peptides or Polypeptides. A peptide or polypeptide is "isolated" if it has been substantially separated from contaminants, e.g., cellular components (nucleic acids, lipids, carbohydrates, and other peptide species) that may accompany it during purification. Such a peptide or polypeptide can also be referred to as "pure" or "homogeneous" or "substantially pure or homogeneous." For example an AIP is isolated when at least 60–90% by weight of a sample is composed of the peptide, preferably 95% or more, and more preferably more than 99%. Purity or homogeneity is determined using conventional assay techniques, such as polyacrylamide gel electrophoresis (PAGE) of a protein sample, followed by visualization of a single polypeptide band upon staining the polyacrylamide gel with a suitable reagent, or by high pressure liquid chromatography (HPLC).

AIP Moieties Having a Non-native Sequence. Preferably, a modification to a natural AKAP sequence consists of a "conservative" amino-acid substitution. "Conservative" amino acid substitutions include those listed in Table 2, below.

TABLE 2

| Original Residue | Conservative Substitutions |
| --- | --- |
| Alanine (A) | G |
| Arginine (R) | K |
| Asparagine (N) | Q, H |
| Aspartic Acid (D) | E |
| Cysteine (C) | S |
| Glutamic Acid (E) | D |
| Glycine (G) | A |
| Glutamine (Q) | N, H |
| Histidine (H) | N, Q |
| Isoleucine (I) | L, V |
| Leucine (L) | I, V |
| Lysine (K) | R |
| Methionine (M) | L, I |
| Phenylalanine (F) | L, Y |
| Proline (P) | G |
| Serine (S) | T |
| Threonine (T) | S |
| Tryptophan (W) | F, Y |
| Tyrosine (Y) | W, F |
| Valine (V) | L, I |

"Non-conservative substitutions" are amino acid substitutions which produce a peptide which reduces binding of a particular second protein (such as PKA) to a first protein (such as an AKAP) by at least about 50%, compared to a peptide (such as an AIP) having a sequence homologous to that of the binding domain of the first protein. Preferably, such substitutions reduce binding by 25% or less, more preferably have no effect on binding, and most preferably improve binding. Nonconservative substitutions can result from changes in: (a) the tertiary structure of the peptide; (b) the charge or hydrophobicity of the peptide; or (c) the bulk of an amino acid side chain. Substitutions generally expected to produce the greatest changes in protein properties are those in which: (a) a generally hydrophilic amino acid residue is substituted for, or by, a generally hydrophobic amino acid residue; (b) a proline residue is substituted for, or by, any other residue; or (c) an amino acid residue having a bulky side chain, e.g., a phenylalanine residue, is substituted for, or by, a residue not having such a side chain, e.g., a glycine residue. Preferably, an amino acid residue having a generally electropositive side chain, e.g., a lysine, arginine, or histidine residue, is not substituted for, or by, a residue having a generally electronegative side chain, e.g., a glutamine or aspartic acid residue.

Alkyl AIP Amides. An alkyl AIP amide is a form of the alkyl peptide amides of this invention produced by linking an alkyl group to the N-terminus of an AIP as described above. The most preferred form of the alkyl AIP amide is a stearyl AIP amide, wherein the alkyl moiety most preferably comprises a straight chain, saturated, alkyl group of 18 carbon atoms in length. In their most preferred form, the alkyl AIP amides of this invention are able to permeate cell membranes (e.g., sperm-cell membranes) and affect binding of PKA to an AKAP within the intracellular spaces of the cell.

The most preferred form of the alkyl AIP amides of the present invention are preferably delivered in such a way that PKA activity is affected only or primarily in target cells, e.g., by topical application, by injection (e.g., into a joint to treat arthritis) or by cell- or tissue-specific delivery of the AIP by methods well known in the art.

Pharmaceutical Compositions. A description of pharmaceutical compositions of this invention is provided below. Particular emphasis is placed on describing compositions of a particularly preferred form of the alkyl peptide amides of this invention, viz., alkyl AIP amides capable of inhibiting sperm motility and their use in contraceptive compositions. However, most of the teachings below, even those specifically directed to specialized contraceptive compositions, can be applied equally to the formulation of pharmaceutical compositions of other alkyl peptide amides of this invention. It is contemplated that the compositions and methods of the present invention will suggest many variations, both human and veterinary, to one skilled in this art.

The present invention encompasses pharmaceutical compositions that include an "effective amount" of an alkyl AIP amide, or mixture of alkyl AIP amides, and one or more non-toxic pharmaceutically acceptable carriers, excipients, diluents, and/or adjuvants. An "effective amount" of an alkyl AIP amide is, e.g., an amount effective to interfere substantially with PKA binding to an AKAP in a target cell, thereby causing at least about a 50%, preferably at least about a 75%, and most preferably at least about a 90% reduction of PKA activity in the cell. For contraceptive compositions, an "effective amount" of an alkyl AIP amide is an amount effective to diminish sperm motility by at least about 50%, preferably at least about 70%, more preferably at least about 80%, and most preferably at least about 90%.

The dosage rate, e.g., 0.05 to about 20 mg/kg of body weight, is a function of the nature and body weight of the human or animal subject to be treated. The dosage unit of any biologically active substance delivered to a subject depends, for example, on the condition treated, nature of the formulation, nature of the condition, embodiment of the claimed pharmaceutical compositions, mode of administration, and condition and weight of the patient, and the activity of the particular substance used. See, e.g., *The Pharmacological Basis of Therapeutics*, Goodman, Gilman, et al., eds., Macmillan, N.Y., 1994, and *Principles of Pharmacology*, Munson et al., ed., Chapman & Hall, New York, 1995. Standard pharmaceutical formulation techniques are preferably used in testing the potency of a given pharmaceutical composition, such as the techniques disclosed in *Remington's Pharmaceutical Sciences*, Mack Publishing Co., Easton, Pa., latest edition.

The pharmaceutical compositions or medicaments of the alkyl peptide amides of the present invention can be formulated for administration by any of various routes. The compositions can be in the form of, for example, tablets, capsules, powders, granules, lozenges, dragées, pills, ampoules, suppositories, or liquid or gel preparations, such as oral, topical, or sterile parenteral solutions or suspensions. In the instance of contraceptives, the medicament is preferably formulated in a suppository, foam, gel, or cream, for example, or applied to a condom, diaphragm, cervical cap, sponge, or other conventional contraceptive barrier prior to intercourse.

Tablets and capsules for oral administration can be in a form suitable for unit-dose presentation and can contain conventional diluents and excipients. The pharmaceutical compositions will generally contain from 0.5 to 90% of the alkyl peptide amide by weight of the total composition. In addition to an alkyl peptide amide or combination of alkyl peptide amides, the pharmaceutical compositions and medicaments can also contain other pharmaceutically active compounds.

For contraceptive use, an alkyl AIP amide or combination of alkyl AIP amides may be combined with one or more other contraceptive substances, e.g., nonylphenoxypolyethoxyethanol (nonoxynol-9), p-diisobutylphenoxypolyethoxyethanol (octoxynol-9), gossypol, gramicidin, neem seed extracts (Praneem), reetha saponins, quinine hydrochloride, etc. Nonoxynol-9 and octoxynol-9 are surface-acting agents that disrupt the cell membrane, thereby killing the sperm cells with which the substances come into contact. The alkyl AIP amide can act in concert with such surface-acting agents by inhibiting sperm motility long enough for the surface-acting agents to come into contact with the sperm cells to kill the cells. Due to the motility inhibition effect of the alkyl AIP amide, contraceptive compositions combining an alkyl AIP amide and, for example, nonoxynol-9, may employ a lower level of nonoxynol-9 than if nonoxynol-9 is used alone. In addition to topical (female) contraceptives, systemic (male) contraceptives are also contemplated in which delivery of an alkyl AIP amide is targeted to an appropriate site to affect sperm motility.

Calcium at sufficient concentrations can overcome the sperm motility inhibition by an alkyl AIP amide. For this reason, a non-toxic chelating agent (such as EDTA or EGTA), or anion that combines with calcium ion to form an insoluble product, such as phosphate, is preferably included in the contraceptive compositions of this invention.

It is further contemplated that the pharmaceutical compositions of this invention will include diluents and/or excipients. Diluents and excipients suitable for use in the pharmaceutical compositions of this invention include: binding agents such as syrup, acacia, gelatins, sorbitol, tragacanth, carboxymethyl cellulose and other cellulose derivatives, alginates, and polyvinylpyrrolidone; fillers and extenders such as sugars, starches, calcium phosphate, sorbitol, mannitol, or glycine; tableting lubricants, such as magnesium stearate, talc, polyethylene glycol or silica; disintegrants, such as potato starch; or acceptable wetting agents, such as sodium lauryl sulfates; and diluents such as water, ethyl alcohol, isopropyl alcohol, ethyl carbonate, ethyl acetate, benzyl alcohol, benzyl benzoate, propylene glycol, 1,3-butylene glycol, dimethylformamide, oils (e.g., ground nut oil), glycerol, tetrahydrofurfuryl alcohol, polyethylene glycols, and fatty acid esters of sorbitol or mixtures thereof. Tablets can be coated by conventional methods.

Pharmaceutical compositions of the present invention may include oral liquid preparations, or dry preparations designed to be reconstituted with water or another suitable vehicle before use. Suitable oral liquid preparations contemplated for inclusion in the pharmaceutical compositions of this invention include preparations in the form of: suspensions, solutions, emulsions, syrups or elixirs. Suitable liquid preparations can also contain conventional additives such as suspending agents, e.g., sorbitol, methyl cellulose, glucose, gelatin, or hydrogenated edible fats; emulsifying agents, e.g., lecithin, sorbitan monooleate, or acacia; non-aqueous vehicles, e.g., almond oil, fractionated coconut oil, oily esters such as glycerine, propylene glycol, or ethyl alcohol; preservatives such as methyl or propyl p-hydroxybenzoate or sorbic acid.

The pharmaceutical compositions of this invention may also include additives, e.g., buffers such as sodium metabisulphite or phosphate buffers; preservatives such as bactericidal and fungicidal agents, including phenyl mercuric acetate or nitrate, benzalkonium chloride or chlorhexidine; thickening agents, such as hypromellose; or flavoring or coloring agents.

The pharmaceutical compositions of this invention, particularly the contraceptive compositions of alkyl AIP amides, can be applied topically. For topical application to the skin, the alkyl peptide amide(s) can be made up into a cream, lotion, or ointment using conventional formulations. For topical applications to the eye, the alkyl peptide amide(s) of this invention can be made up into a solution or suspension in a suitable sterile aqueous or non-aqueous vehicle.

The pharmaceutical compositions of this invention can also be administered parenterally in a sterile medium. The drug can be dissolved or suspended in the vehicle, depending on the vehicle or concentration used. Adjuvants such as local anesthetics, preservatives, and buffering agents can also be dissolved in the vehicle. Commonly used excipients for injectable forms of the pharmaceutical compositions of the present invention include physiological saline, Hank's solution, Ringer's solution, and the like. Injection can be, e.g., intravenous, intramuscular, intraperitoneal, or subcutaneous.

The pharmaceutical compositions of this invention can also be administered by transdermal or transmucosal delivery by including agents which effect penetration of these tissues, such as bile salts, fusidic acid derivatives, cholic acid, and the like.

The invention will be better understood by reference to the following examples, which are intended merely to illustrate the synthesis, purification, and use of alkyl peptide amides of the present invention in two different types of living cells, sperm cells and HeLa cells. However, the scope of this invention is not to be considered limited to the specific species, compositions, and uses of alkyl peptide amides used in the examples below.

EXAMPLE 1

Stearyl Peptide Amide Synthesis and Purification

The peptides described in the examples herein below were all synthesized by Quality Controlled Biochemicals, Inc. (of Hopkinton, Mass. USA), on an automated synthesizer using 9-fluorenylmethoxycarbonyl (FMOC) chemistry employing base-mediated coupling. The activator of choice was either BOP or HATU, using diisopropylethyiamine as a solvent. Stearic acid was added together with an activator of attachment to the free amino-terminus of the protected peptide. The progress of the stearation reaction was monitored by ninhydrin, a TFA test cleave, or by mass spectral or HPLC analysis.

The final stearated peptide product was purified by reverse phase HPLC using a C8 column employing a TFA/acetonitrile buffer system. To identify the correct peak and facilitate recovery of pure material, the molecular weight confirmation of the stearated material was performed using a TOF mass spectrometry analyzer. Analytical HPLC traces of the pooled fractions confirmed the expected purity. Pooled fractions were lyophilized to a dry powder under nitrogen. The stearyl peptide amides constructed and used in the Examples below were as follows:

s-PKI: Stearyl-TTYADFIASGRTGRRNAIHD amide (SEQ ID NO:11)

s-Ht31: Stearyl-DLIEEAASRIVDAVIEQVKAAGAY amide (SEQ ID NO:2)

s-Ht31-P: Stearyl-DLIEEAASRPVDAVPEQVKAAGAY amide (SEQ ID NO:12)

s-AKAP79: Stearyl-YETLLIETASSLVKNAIQLSIE amide (SEQ ID NO:13)

EXAMPLE 2

Inhibition of Hela Cell PKA by a Stearyl PKI Amide

A. Characterization of a cAMP-dependent Protein Kinase Inhibitor Peptide

The PKI peptide described immediately above is known to be a very potent inhibitor, having an $IC_{50}$ for purified PKA in the nanomolar range, and having an $IC_{50}$ for PKA supplied in the form of a cellular extract in the micromolar range. The term "$IC_{50}$" as used herein refers to the concentration of inhibitor required to produce a 50% reductiorin enzyme activity of PKA. The results showed that the stearyl PKI amide, s-PKI, inhibited the enzymatic activity of the catalytic subunit of PKA in cellular extracts in a concentration-dependent manner, and with $IC_{50}$ similar to that for the non-stearated PKI. That indicated the modification of PKI by the addition of stearyl moiety to produce s-PKI as described in Example 1, above, did not alter the inhibitor potency towards PKA (see FIG. 2).

The results above led to experiments designed to test the efficacy of s-PKI on the activity of PKA in vivo. HeLa cells were chosen as the model for these studies. However, any other cell could have been used to test the inhibitory potency of this particular stearyl peptide amide PKI, since PKA is a ubiquitous enzyme. Activation of PKA in any cell is dependent on the availability of the second messenger cAMP. Therefore, any agent that activates or inhibits the enzyme adenylate cyclase will accordingly cause an increase or decrease in the endogenous level of cAMP and thus alter the activity of PKA.

Forskolin, a plant alkaloid, is known to be a potent activator of adenylate cyclase in HeLa cells, resulting in a significant increase in the endogenous level of cAMP. This agent was employed in the studies reported herein, by adding it to the medium at a concentration known to be sufficient to significantly increase the amount of cAMP in HeLa cells. The HeLa cells used in this study were grown in a mixture of Dulbecco's Modified Eagle Medium (DMEM) and fetal bovine serum (FBS), containing either 100 $\mu$M of forskolin, or an equal volume of DMSO as a vehicle control.

When the unmodified PKI was tested against PKA and compared with that of s-PKI, it was found that s-PKI inhibited the enzymic activity of PKA in vivo in HeLa cells within sixty minutes after addition of the inhibitor to the medium and the inhibition was observed for both basal (no forskolin) and forskolin-stimulated cells. In contrast, the unmodified non-stearated PKI did not have any significant inhibitory effect on the enzyme activity of PKA.

B. Effect of Concentration of s-PKI Used to Treat HeLa Cells

Cultures of HeLa Cells were treated with differing amounts of s-PKI, in the presence or absence of forskolin, as follows. About $10^6$ HeLa cells were incubated in a 75 centimeter-squared ($cm^2$) flask containing 5 milliliters (ml) DMEM/10% FBS medium in the presence of 0, 10, 25, 50, and 100 micromolar ($\mu$M) s-PKI for thirty (30) minutes. The cells were then transferred to a medium solution (DMEM/ 10% FBS) supplemented with either forskolin (100 $\mu$M) or an equal volume of vehicle control (0.1% DMSO), and incubated for an additional 30 minutes.

At the end of the second 30 minutes, the cells were harvested and processed, as follows: The cells were first washed to remove any adhering inhibitor or other adherent material, and then scraped into serum-free DMEM. The resulting scraped cells were then lysed in lysis buffer, thereby forming a lysate. The lysate was centrifuged and the supernatant was used to assay the PKA kinase activity as described by Goueli, et al (*Anal. Biochem.* 225: 10–17, 1995). Protein concentration was determined using the assay protocol described in the aforementioned reference, which is incorporated by reference herein.

The results of this assay are displayed in Table 3, below.

TABLE 3

| s-PKI Concentration ($\mu$M) | PKA activity (pmoles $^{32}$P/min/$\mu$g protein) | Percent Inhibition |
|---|---|---|
| 0 | 3.258 | 0 |
| 10 | 2.536 | 22 |
| 25 | 2.456 | 25 |
| 50 | 1.775 | 45 |
| 100 | 0.80 | 75 |

C. Effect of Incubation Time in Presence of s-PKI on HeLa Cells

Table 4, below, presents the results of a specific study done to determine the effect of incubation time of s-PKI on the kinase activity of PKA in HeLa cells. HeLa cells were grown in medium supplemented with s-PKI for varying amounts of time, and the inhibitory effect on PKA kinase activity was measured. HeLa cells ($10^6$ cells per dish) were grown in DMEM medium supplied with 10% FCS and fresh medium was added with and without inhibitor (s-PKI) for various periods (0, 1, 2, and 3 hours) with and without the addition of 100 $\mu$M of forskolin 30 minutes before harvesting the cells.

The harvested cells were then processed, and the PKA kinase activity was assayed as follows. The medium was removed and the cells were washed in fresh medium several times and then lysed using a lysis buffer. The lysate was centrifuged and the supernatant was used to assay the PKA kinase activity as described by Goueli et al. (1995) *Anal. Biochemistry* 225: 10–17. Protein concentration was determined using published protocols

TABLE 4

| Incubation Time (hr.) | PKA Activity (pmoles $^{32}$P/min/µg protein) | Percent of Activity Remaining |
|---|---|---|
| 0 | 2.84 | 0.0 |
| 1 | 1.432 | 50.4 |
| 2 | 1.791 | 63.0 |
| 3 | 1.996 | 70.3 |

The data in Table 4 demonstrate that s-PKI lost its effectiveness as an inhibitor after a few hours in the medium. The presence of forskolin was found to have no effect upon activity. These results could indicate that s-PKI was degraded in the medium by an exogenous or secreted protease (or esterase), or that it was degraded intracellularly.

The apparent loss in effectiveness of s-PKI as an inhibitor of PKA activity over time could have been accounted for and counteracted in any one of a number of ways. For example, s-PKI could have been added to the medium every few hours, and the medium replenished more frequently than it was in this Example. Alternatively, a new stearyl peptide amide could have been designed with a subset of the sequence of PKI, so the resulting modified form of s-PKI could have survived degradation, thus remaining intact in the medium and in the cells for longer periods of time.

EXAMPLE 3

Sperm Motility Assays

A. Materials and Methods

Sperm Preparation. Testes from mature bulls with intact tunica were obtained from a local slaughterhouse and sperm from caput or caudal epididymis were isolated and washed as previously described (Vijayaraghavan et al., *Biol. Reprod.* 32:489–500, 1985). The sperm were resuspended in buffer A (120 mM NaCl, 10 mM KCl, 10 mM Tris[hydroxymethyl] aminomethane (TRIS), pH 7.4) supplemented with 10 mM glucose and 10 mg/ml bovine serum albumin (BSA) for motility measurements. Monkey semen was obtained by electro-ejaculation and processed by procedures previously reported (Smith et al., *Biol. Reprod.* 54:719–727, 1996). Human semen samples were obtained from a fertility clinic at the Oregon Health Sciences University.

Sperm Motility Measurement. Head motility parameters were determined as previously described (Vijayaraghavan et al., *Biol. Reprod.* 54:709–718, 1996; Stephens et al., *Biol. Reprod.* 38:577–586, 1988). A 3–4 µL aliquot of sperm suspension (5×10$^7$/ml) was loaded onto a counting chamber at 37° C. After bulk fluid movement had subsided, six different locations on the slide were recorded. The video-taped segments were analyzed by a computerized image-analysis system (CASMA) as previously described (Vijayaraghavan et al., *Biol. Reprod.* 54:709–718, 1996; Stephens et al., *Biol. Reprod.* 38:577–586, 1988). This computer system measured several parameters of head motion, including forward motility. The forward Motility Index (FMI) was used as the measure of motility. FMI is a product of percent motile (%M, percent of sperm moving at velocity greater than 20 mm/sec) and average velocity (Va, the five-point smoothed average of the head positions through analysis of at least twenty frames). In most cases both components of FMI were found to increase together.

PKA Activity. PKA activity was assayed as previously described (Carr et al., *J. Biol. Chem.* 268:20729–20732, 1993) with minor changes. Whole caput or caudal sperm were treated with 2-chloro-2'-deoxyadenosine (50 µM), H-89 (50 µM), or both for 30 min. at 37° C. The sperm were then washed twice in ice cold homogenization buffer supplemented with protease inhibitors, benzamidine (10 mM), leupeptin (4 µg/ml), and N-tosyl-L-phenylalanine chloromethyl ketone (TPCK) (100 µM), and sonicated for one min. Reaction mixtures (20 microliters (µl) total) contained 250 µM Kemptide (i.e., LRRASLG), 250 µM (γ$^{32}$P) ATP, 25 mM Na$_3$VO$_4$, 50 mM 3-[N-morpholino] propanesulfonic acid (MOPS) (pH=7.0), 10 mM MgCl$_2$, 0.25 mg/ml BSA and where indicated, 10 µM cAMP. Assays were initiated by addition of labeled ATP, incubated for 2 min at 30° C., and stopped by addition of 30 µl of 1 N HCl. Twenty µl of the reaction was then spotted on phosphocellulose paper followed by three washes in 75 mM phosphoric acid. The papers were then analyzed by Cerenkov counting. All determinations were made in quadruplicate.

Western blotting and overlay assays. The overlay procedure is a modified Western blot procedure. Proteins were separated by SDS-polyacrylamide gel electrophoresis (SDS-PAGE) and transferred to a nylon membrane (Immobilon). After treatment with Blotto (*Protein Methods*, Bollag and Edelstein, eds., Wiley-Liss, New York, 1991) to prevent non-specific binding, radiolabelled RIIα or RIIβ probes were applied (Carr and Scott, *Trends Biochem. Sci.* 17:246–249, 1992). Recombinant RIIα was produced as previously described (Carr et al., *J. Biol. Chem.* 266:14188–14192, 1991; Carr et al., *J. Biol. Chem.* 267:13376–13382, 1992). RIIα and RIIβ were gifts from Dr. John Scott, Oregon Health Sciences University, Portland, Oreg. Two different variations of the overlay assay were used. In the first variation, recombinant RII radiolabeled by incubation with the catalytic subunit of PKA and γ$^{32}$P-ATP was used. After separation from free γ$^{32}$P-ATP, the $^{32}$P-labeled RII (500,000 CPM/10 ml blotto) was incubated with the blocked blot for four hours followed by washing and autoradiography. In the second variation, the blot was incubated with cold RIβ (1 µg/10 ml Blotto), washed, then incubated with anti-RIβ antiserum. After the blot was again washed, it was incubated with secondary antibody conjugated to horseradish peroxidase. A final wash was followed by development with an enhanced chemiluminescence kit (Renaissance™, New England Nuclear). The PKA isoform-specific antibodies were affinity-purified antibodies obtained from Triple Point Biologics, Forest Grove, Oreg.

B. Results

Identification of AKAPs and PKA isoforms in Bovine, Human and Monkey Sperm.

Cyclic AMP has been known to stimulate sperm motility in a variety of species. To determine if PKA anchoring is involved in regulating motility, the PKA isoforms and AKAPs present in mammalian sperm were identified. Immunoblot analysis of sperm proteins with affinity-purified, isoform-specific antibodies detected three (RIIα, RIIβ, and RIβ) of the four known PKA isoforms in bovine, human and monkey sperm (FIG. 3).

FIG. 3 shows the results of identifying PKA subunits in various mammalian sperm. Sperm from bovine (B), human (H) and monkey (M), were lysed and the proteins were separated by SDS-PAGE and analyzed by Western blotting for regulatory subunits of PKA (RIα, RIβ, RIIα, or RIIβ) using isoform specific antibodies.

No RIα was detected at the 50 to 55 kDa range in sperm from any of the species, even though RIα was detectable in bovine testis. The lower Mr bands detected in bovine and human sperm with anti-RIα antibody might be breakdown products of RIα. However, the other isoforms showed very little apparent proteolysis. The fuzziness of the bands detected with the RIIα and RIβ antibodies suggest that these proteins may be at least partially phosphorylated.

Identification of PKA isoforms in three different species of sperm using four different antibodies.

To determine if the PKA isoforms are associated with the soluble or insoluble fractions of sperm sonicates, bovine sperm were homogenized, centrifuged at 16,000×g for 30 min and subjected to western blot analysis (FIG. 4). Bovine caudal epididymal sperm were lysed by sonication, separated into supernatant (S) or pellet (P) fractions by centrifugation at 16,000×g, and probed using anti-RIIα, anti-RIIβ and anti-RIβ antibodies.

Greater than 50% of all three R subunit isoforms are present in the pellet fraction of sperm sonicates, and RIβ is found almost exclusively in this fraction. These results suggest that all of these isoforms are associated with structural or cytoskeletal elements of the sperm.

Overlay analysis of bovine, human and monkey sperm using $^{32}$P-labeled RIIα or RIIβ as probes detected a single dominant AKAP in each species (FIG. 5). A single predominant AKAP was detected in bovine, human, and monkey sperm using either RIIα or RIIβ as a probe. The bovine and human AKAPs had relative molecular weights of 110 kDa, while the monkey AKAP was slightly larger, at a relative molecular weight of 115 kDa. The overlay assay also detects the endogenous RII isoforms accounting for the bands observed at 55 kDa.

The bands detected at approximately 55 kDa by the RIIβ probe are probably due to dimerization of the probe with endogenous RII, although it is not clear why these proteins are preferentially binding to RIIα compared to RIIβ. Overlay analysis using RIβ did not detect any binding proteins. These data suggest that a single AKAP in sperm may be responsible for the localization of both RIIα and RIIβ. The fact that RIβ is clearly present in the particulate fraction, but does not interact with denatured proteins on the blot, suggests that the overlay method may not be appropriate or detecting AKAPs that interact with RII. Instead, a non-denaturing binding assay, such as a band-shift assay (Carr and Scott, Trends Biochem. Sci. 17:246–249, 1992) may be used for detecting RI-binding proteins.

All AKAPs identified to date contain an amphipathic helix domain responsible for RII binding (Carr et al., *J. Biol. Chem.* 266:14188–14192, 1991; Carr et al., *J. Biol. Chem.* 267:13376–13382, 1992; Carr et al., *J. Biol. Chem.* 267:16816–16823, 1992; Coghlan et al., *J. Biol. Chem.* 269:7658–7665, 1994; McCartney et al., *J. Biol. Chem.* 270:9327–9333, 1995; Carr et al., *J. Biol. Chem.* 267:13376–13382, 1992). A peptide, Ht31, containing an amphipathic helix domain, binds to RII and competitively inhibits the interaction of RII with other AKAPs. Addition of this AIP to the overlay assay blocked RII binding with AKAP 110 (FIG. 6), suggesting that this sperm AKAP also contains an amphipathic helix-binding domain. A cell-permeable stearated Ht31 counterpart, N-St Ht31, also inhibited in vitro binding of RII to AKAP 110, albeit at a reduced potency (85% inhibition s compared with 100% by the non-stearated Ht31). The control stearated peptide, s-Ht31-P, which has a proline substitution preventing amphipathic helix formation, had no effect on RII binding.

FIG. 6 shows the results of disrupting the binding of RII to sperm AKAPs by an AIP, or by a control alkyl peptide amide. RII overlays were performed in the absence (lane 1) or presence of 20 μM Ht31, s-Ht31, or s-Ht31-P (lanes 2, 3 or 4, respectively). Addition of the three peptide species inhibited RII binding to AKAP110 by 100%, 85% and 0%, respectively, as determined by densitometric scanning analysis.

Effect of Stearyl AIP Amides on Sperm Motility. Stearyl AIP amides, such as s-Ht31 or s-AKAP79 were added to vigorously motile sperm under a variety of conditions to determine whether PKA anchoring would be sufficiently inhibited to produce a reduction in sperm motility. The results, shown below, indicated that each stearyl AIP amide tested inhibited basal motility in a concentration- and time-dependent manner.

In the first such experiment, the vital dyes SYBR-green and rhodamine 123 were added to sperm before and after treatment with s-Ht31 in order to determine whether s-Ht31 affects sperm viability or structural integrity. Only viable, intact cells normally take up such dyes. Both treated and control sperm were found to accumulate these dyes to the same extent, suggesting that the stearyl peptide amide (s-Ht31) did not decrease viability or disrupt the integrity of the sperm plasma membrane. In experiments using sperm loaded with the chromophores BCECF or Fura 2, addition of digitonin, but not s-Ht31, caused release of these dyes, confirming that peptide treatment did not compromise the integrity of the plasma membrane.

FIG. 7 summarizes the results of the second such experiment. This second experiment was conducted as follows. Sperm were incubated in buffer A containing s-Ht31 at 5 μM (●), 10 μM (■) or 50 μM (♦) or a control peptide, s-Ht31-P at 50 μM (x). Motility was assayed at the times indicated by computer-automated sperm motility analysis (CASMA) as described previously. Complete arrest of motility was observed at concentrations from 5 to 50 μM within three to five minutes after treatment (FIG. 7).

FIG. 8 is a plot of the results of experiments in which sperm were incubated for 5 min in buffer A containing increasing concentrations of s-Ht31 (♦) or control peptide s-Ht31-P (▲) and the motility index was determined. When motility is measured five minutes post-treatment, the concentration of s-Ht31 needed to produce 50% inhibition is approximately 1 μM (FIG. 8). A control peptide, s-Ht31-P, which is ineffective in disrupting PKA anchoring to AKAPs (see FIG. 6), had no effect on sperm motility at concentrations up to 20 μM, suggesting that motility inhibition by s-Ht31 was due to disruption of PKA anchoring.

The next experiments in this set demonstrated that sperm with inhibited motility after exposure to s-Ht31 could regain full motility after contact with s-Ht31 ceased, at least under certain conditions. In each such experiment, sperm motility was monitored 5, 30, and 60 minutes after exposure to s-Ht31 in the presence of buffers with various salt compositions. FIG. 9 shows sperm motility recovery results from bovine caudal epididymal sperm suspended in buffer A supplemented with 2 mM calcium (+Calcium) or 2 mM EGTA (−Calcium), after treatment with water (control) or with 10 μM s-Ht31. The results of this first experiment (shown in FIG. 9) demonstrated the motility of sperm treated with s-HT31 only recovered after treatment when the sperm were suspended in calcium-containing media. When the sperm were suspended in a medium depleted of external calcium, by the addition of EGTA, treatment with s-Ht31 caused irreversible motility arrest. The presence or absence of external calcium did not affect the motility of untreated sperm.

Sperm motility and motility inhibition by s-Ht31 was also assayed in the presence and absence of bicarbonate. Bicarbonate was used in this experiment because of its demonstrated tendencies to stimulate sperm adenyl cyclase (Okamura et al., *J. Biol. Chem.* 260:9699–9705, 1985), and to increase intracellular pH (Vijayaraghavan et al., *Biol. Reprod.* 32:489–500, 1985). Bicarbonate has also been described as an essential component of suspension buffers required for optimal sperm function in vitro (Lee and Storey, Biol. Reprod. 34:349–356, 1986; Kopf and Gerton, in *Elements of Mammalian Fertilization*, Wassermann, ed., pp. 153–203, CRC Press, Boca Raton, Fla., 1991).

FIG. 10 shows the results of this last experiment. In the experiment, sperm were incubated in buffer A containing 2 mM calcium and 50 mM bicarbonate (where indicated). Motility was assessed at 5, 30 and 60 min following addition of either water (control) or 10 µM s-Ht31. Sperm motility in the presence of bicarbonate is significantly enhanced compared to untreated sperm (FIG. 10). To determine the effect of AIPs on optimal motile sperm, s-Ht31 was added to sperm in both basal and bicarbonate-supplemented media (FIG. 10). The peptide was equally effective in inhibiting motility in both media. Similar results were obtained when sperm were pretreated with other activators of motility, dibutyryl cyclic 3',5'-adenosine monophosphate (db-cAMP), isobutyl-methylxanthine (IBMX), and CDA, all thought to increase cAMP content.

In similar experiments, addition of the same stearyl AIP amide (s-Ht31) to undiluted rhesus monkey (FIGS. 11 and 12) and human ejaculated semen (FIG. 13) was likewise found to result in a reduction in sperm motility. The experiments and figures displaying this last set of results are summarized further below.

FIG. 11 shows the effect of s-AKAP79 on the motility of monkey-ejaculate sperm at 5 min (light gray bar) and 30 min (dark gray bar). Increasing concentrations of s-AKAP79 were added to neat monkey semen and incubated at 37° C. Motility was assayed at 5 and 30 min. As was observed in the s-Ht31 studies described above, the results of this experiment showed s-AKAP inhibited sperm motility in a concentration- and time-dependent manner.

FIG. 12 shows the effect of s-Ht31 on the motility of monkey semen and swim-up sperm. Monkey sperm, either neat semen or semen collected after swim-up analysis, were incubated with no addition (Control) (open bar), 50 µM s-Ht31 (solid bar), 2.5 mM EGTA (hatched bar) or 2.5 mM EGTA plus 50 µM s-Ht31 (dotted bar). Motility was assayed after 15 min.

FIG. 13 shows the effect of s-Ht31 on the motility of human-ejaculate swim-up sperm. Human sperm collected after swim-up analysis were incubated for 15 min with no addition (Control), 100 µM s-Ht31, or 100 µM s-Ht31-P and assessed for motility.

Role of PKA in sperm motility and s-Ht31 action. If the effect of anchoring inhibitor peptides on sperm motility is due to the dissociation of the catalytic subunit of PKA from its preferred substrates, then this effect should be mimicked by inhibitors of PKA activity. To test this hypothesis, the effect of a potent cell-permeable PKA inhibitor, N-[2-(p-bromocinnamylamino)ethyl]-5-isoquinoline-sulfonamide (H-89), on sperm motility was studied.

FIG. 14 shows the effect of H-89 on sperm motility and PKA activity from control sperm and sperm activated by 2-chloro-2'-deoxyadenosine (CDA). Bovine caudal and caput sperm were incubated in buffer A in the presence or absence of 50 µM CDA and/or 50 µM H-89. When sperm were treated with both CDA and H-89, the H-89 was added 15 min prior to CDA. Motility was assessed by CASMA at 15 min following treatment. Addition of high levels of H-89 (50 µM) inhibited basal sperm motility approximately 50% or less, and had no effect on sperm motility stimulated by the adenosine analog CDA (FIG. 14).

Essentially identical data to the data shown in FIG. 14 were obtained when sperm were stimulated with isobutyl-methylxanthine (IBMX) or 8-bromo-cAMP (8-Br-cAMP) instead of CDA (FIG. 15). This unexpectedly weak action of H-89 apparently results primarily from a decrease in motility of a subpopulation of sperm, because a considerable proportion of sperm maintain vigorous motility. This contrasts sharply with the complete arrest of motility seen in S-Ht31 treated sperm. Also, unlike the action of the alkyl AIP amides, the effects of H-89 were strongly suppressed by CDA. The effectiveness of H-89 was also observed with caput sperm, which are immotile unless stimulated with agents such as CDA or IBMX. Motility induction by CDA is unaffected by preincubating sperm with H-89 before treatment (FIGS. 14 & 15). Together these observations suggest that AIPs and PKA kinase inhibitors, have different mechanisms of action.

In previous reports, initiation or stimulation of sperm motility by CDA was associated with an elevation of cAMP and an increase in PKA activity was assumed (Vijayaraghavan and Hoskins, *Biol. Reprod.* 34:468–77, 1986). Because H-89 failed to suppress stimulation of motility by CDA, PKA activity from caudal and caput sperm which had been treated with CDA, H-89 or CDA plus H-89 was measured. All assays were performed in the absence or presence of cAMP to determine the basal and maximal PKA activities. Bovine sperm were incubated as described for FIGS. 14 and 15 and then assessed for PKA activity. Where indicated, 10 µM cAMP was added to the PKA assay. The results of this assay are shown in FIG. 15.

Treatment with CDA increased basal PKA activity by approximately 60% in both caudal and caput sperm. H89 treatment, in the presence or absence of CDA, strongly inhibited PKA activity. Addition of cAMP to the assay was not able to overcome this inhibition. To ensure that H-89 was affecting PKA activity in the cells and not just its activity in the in vitro assay, the sperm were washed several times before lysis to remove all exogenous H-89. PKI (50 µM), a non-permeable PKA inhibitor, was added as a control to sperm. The sperm were then washed, lysed and assayed for PKA activity in a manner identical to the H-89 treated sperm. PKI had no effect on cellular PKA activity, although a similar concentration, when added to the PKA assay, will inhibit virtually 100% of activity. These data suggest that motility stimulation associated with treatments that elevate cAMP does not require increases in the catalytic activity of PKA and can occur even if PKA activity is substantially inhibited.

Finally, FIG. 16 shows the effect of s-Ht31, s-AKAP79, and s-Ht31-P on the motility of bovine sperm. Sperm were incubated for 5 min in buffer A containing increasing concentrations of s-Ht31 (diamonds), s-AKAP79 (squares) or control peptide s-Ht31-P (triangles) and motility was assessed.

C. Discussion

As an initial step in studying the role of PKA anchoring in regulation of sperm function, PKA isoforms and AKAPs that are present in mammalian sperm were identified. Three of the four isoforms of the regulatory subunit of PKA were detected in bovine, human and monkey sperm. RIα, though abundant in testis, were not detected in sperm. Consistent with previous reports (Horowitz et al., *J. Biol. Chem.* 263:2098–2104, 1988), the major proportion of all isoforms remained in the particulate fraction, presumably due to their interaction with AKAPs. The Examples described above also demonstrated bovine, human and monkey sperm each contain one predominant AKAP with an apparent molecular weight between 110 and 115 kDa. The Examples also demonstrated that AKAPs of each such organism studied predominately localized to the particulate fraction and bound to both RIIα and RIIβ, suggesting that a single AKAP is responsible for the localization of both these RII isoforms. In the overlay assays described above, in which RIβ was used as a probe, no binding protein was deleted in any of the sperm studied. The fact that RIβ was clearly in the particulate fraction in Example, but does not interact with denatured proteins on the blot, suggests that the overlay procedure may not be appropriate for detecting AKAPs that interact with RIβ. Preliminary analysis by electron microscopy detects RIIβ in both the head and tail, while RIIα is almost exclusively associated with the axoneme.

In accord with these observations, Orr and colleagues reported one predominant AKAP at molecular weight of approximately 120 kDa in bovine sperm (Horowitz et al., *J. Biol. Chem.* 263:2098–2104, 1988), and Rubin and colleagues found a single RIIβ AKAP (~120 kDa) that binds RIIβ in mature mouse sperm (Lin et al., *J. Biol. Chem.* 270:27804–27811, (1995)). Others, however, have reported RIIα-binding AKAPs of 82 kDa in mouse that bind RIIα (Carrera et al., *Dev. Biol.* 165:272–284, 1994), 80 kDa in rat (Horowitz et al., *J. Biol. Chem.* 263:2098–2104, 1988) and 72 kDa in human (Pariset and Weinman, *Mol. Reprod. Develop.* 39:415–422, 1994). The reason for these differences is not clear, although proteolysis is one possibility. Prolonged storage of SDS-solubilized extracts was found to result in loss of the 110-kDa band and the appearance of an 80-kDa band. The 72-kDa RIIα-binding band reported in human sperm (Pariset and Weinman, *Mol. Reprod. Develop.* 39:415–422, 1994) is distinct from all other known AKAPs due to the fact that it was detected using a peptide from RIIα (amino-acid residues 45–75) which does not contain the AKAP-binding domain (Luo et al., *J. Biol. Chem.* 265:21804–21810, 1990; Scott et al., *J. Biol. Chem.* 265:21561–21566, 1990; Hausken et al., *J. Biol. Chem.* 269:24245–24251, 1994; Li and Rubin, *J. Biol. Chem.* 270:1935–1944, 1995). Finally, the cloning of a sperm AKAP of 84 kDa that is uniquely expressed during spermatogenesis has been reported (Lin et al., *J. Biol. Chem.* 270:27804–27811, 1995). This AKAP is not found in mature sperm and thus its relationship, if any, to AKAP 110 in mature sperm is unknown. To date, only sperm cells have been shown to contain an AKAP of 110 kDa.

Several reports have suggested that flagellar activity in sperm is regulated by cAMP (Tash, *Cell Motil. Cytoskel.* 14:332–339, 1989; Garbers and Kopf, in *Advances in Cyclic Nucleotide Research*, Greengard and Robison, eds., Vol. 13, pp. 252–306, Raven Press, New York, 1980; Lindemann and Kanous, *Arch. Androl.* 23:1–22, 1989; Tash and Means, *Prog. Clin. Biol. Res.* 267:335–355, 1988). Both PKA and AKAPs have been shown to be located at the same subcellular site in sperm, the outer mitochondrial membrane located on the proximal flagella (i.e., the sperm "midpiece") (Lieberman et al., *J. Cell Biol.* 107:1809–1816, 1988; Lin et al., *J. Biol. Chem.* 270:27804–27811, 1995). Addition of a cell-permeable AIP dramatically inhibits sperm motility in a dose- and time-dependent manner. This inhibition is reversible, but only in the presence of external calcium, suggesting that the regulatory mechanism being disrupted may involve maintenance of calcium homeostasis or a calcium-regulated function that recovers only in the presence of exogenous calcium. Since mitochondria play an important role in sperm calcium homeostasis (Babcock et al., *J. Biol. Chem.* 251:3881–3886, 1976; Vijayaraghavan and Hoskins, *Cell Calcium* 10:241–253, 1989; Vijayaraghavan et al., *Biol. Reprod.* 40:744–751, 1989; Vijayaraghavan and Hoskins, *Mol. Reprod. Develop.* 25:186–194, 1990; Vijayaraghavan et al., *Mol. Reprod. Dev.* 38:326–333, 1994), it is reasonable to propose that disruption of RII anchoring in this region could be responsible for the changes in sperm $Ca^{2+}$ regulation. The control peptide, s-Ht31-P, had no effect on motility, suggesting that motility inhibition by s-Ht31 was not due to the stearate moiety but due to disruption of PKA anchoring. Reversibility of the motility inhibition and the observations that s-Ht31-treated sperm exclude vital dyes provide evidence that the motility inhibition is not due to disruption of sperm plasma membrane integrity. The simplest model consistent with these data is that the interaction of the regulatory subunit of PKA with AKAP 110 is essential for sperm movement.

It is usually assumed that the main function of this interaction is to translocate the catalytic subunit to a preferential subcellular site for specific phosphorylation of protein substrates in the vicinity. This model is supported by studies showing that microinjection of AIPs into neuronal or muscle cells mimics the effect of PKA inhibitors causing loss of cAMP modulation of the glutamate receptor and voltage-gated calcium channels (Rosenmund et al., *Nature* 368:853–856, 1994; Johnson et al., *Proc. Natl. Acad. Sci. USA* 91:11492–11496t 1994). FIGS. 14 and 15 demonstrate that in sperm inhibition of the kinase activity of the catalytic subunit of PKA does not mimic the effect of AIPs, suggesting that the interaction of the regulatory subunit with sperm AKAPs has regulatory actions independent of the catalytic subunit. Others have also suggested that the regulatory subunit acts independently of the catalytic subunit (De Camilli et al., *J. Cell Biol.* 103:189–203, 1986). An independent role of RII in the regulation of sperm motility has also been suggested by reports showing that the addition of axokinin (later shown to be RII) [Noland et al., *Biol. Reprod.* 37:171–180, 1987; Paupard et al., *J. Cell. Biochem.* 37:161–175, 1988] to demembraned sperm was sufficient to induce motility (Tash et al., *Cell* 38:551–559, 1984; Tash et al., *J. Cell Biol.* 103:649–655, 1986; Tash and Bracho, *J Androl.* 15:505–509, 1994).

Even though the activation of motility agents which increase sperm cAMP is well substantiated, the role of PKA has never been clear. For instance, PKA inhibitors reportedly do not alter the stimulatory actions of cAMP on motility of intact or demembranated sperm (Carr and Acott, *Biology of Reproduction* 43:795–805, 1990; San Agustin and Witman, *Cell Motility & the Cytoskeleton* 27:206–18, 1994). These reports, however, did not conclusively establish that the PKA inhibitors were indeed inhibiting sperm PKA. Assay results reported herein demonstrate that under conditions where sperm PKA is clearly inhibited, compounds that elevate cAMP such as CDA, IBMX, and 8-Br-cAMP still induce or stimulate sperm motility. The lack of effect of H-89, even at concentrations as high as 50 μM, on cAMP-mediated induction and stimulation of motility is quite unequivocal. These data suggest that the association of RII with AKAPs, but not PKA catalytic activity, is required for sperm motility. Therefore, RII, independent of PKA activity, may regulate other biochemical events such as phosphatase activity and intracellular ion concentration.

This regulation may involve protein-protein interaction between the RII/sperm AKAP complex and other sperm proteins. The demonstration that the phosphatase PP2B, PKA, and PKC are all anchored to the same AKAP in neurons (Klauck et al., *Science* 271:1589–1592, 1996) opens up several possible, previously unidentified, roles for the individual members of this multimeric complex. The interaction between RII and other sperm proteins could also be cAMP-dependent, since cAMP is known to produce a conformational change in the regulatory subunit. The data presented herein show that RII anchoring, independent of PKA catalytic activity, is essential for sperm motility and that cell-permeable AIPs disrupt PKA anchoring and cellular function.

All publications and published patent documents cited in this specification are incorporated herein by reference to the same extent as if each individual publication or patent application was specifically and individually indicated to be incorporated by reference.

Having illustrated and described the principles of the present invention, it should be apparent to persons skilled in the art that the invention can be modified in arrangement and detail without departing from such principles. All modifications that are within the spirit and scope of the invention are to be included within the scope of the invention as described herein.

I claim:

1. A method of reducing motility in sperm cells comprising the step of:
 contacting the sperm cells with at least one alkyl peptide amide in an amount effective to reduce sperm cell motility relative to sperm cells not exposed to the alkyl peptide amide, the alkyl peptide amide comprising:
 an alkyl moiety comprising at least 12 carbon atoms;
 a peptide moiety comprising at least 4 amino residues; and
 an amide bond linking the alkyl moiety and the N-terminus of the peptide moiety;
wherein the peptide moiety reduces or inhibits binding of cAMP-dependent protein kinase A by A-kinase anchoring protein.

2. The method of claim 1, wherein the alkyl moiety comprises at least eighteen (18) carbon atoms.

3. The method of claim 2, wherein the alkyl moiety is a stearyl group.

4. The method of claim 1, wherein the peptide moiety comprises an amino acid sequence homologous to an A-kinase anchoring protein amino acid sequence capable of binding cAMP-dependent protein kinase A.

5. The method of claim 4, wherein the peptide moiety comprises a sequence selected from the group consisting of: SEQ ID NO:3, SEQ ID NO:4, SEQ ID NO:5, SEQ ID NO:6, SEQ ID NO:7, SEQ ID NO:8, SEQ ID NO:9, and SEQ ID NO:10.

6. The method of claim 1, wherein the alkyl peptide amide is supplied as a pharmaceutical composition comprising the alkyl peptide amide and a pharmaceutically acceptable carrier.

7. The method of claim 6, wherein the pharmaceutical composition further comprises a chelating agent.

* * * * *